(12) United States Patent
Rowen

(10) Patent No.: US 11,739,873 B2
(45) Date of Patent: Aug. 29, 2023

(54) SYSTEMS AND METHODS FOR A REUSABLE, ASEPTIC CONNECTOR

(71) Applicant: CENTRE FOR COMMERCIALIZATION OF REGENERATIVE MEDICINE, Toronto (CA)

(72) Inventor: Moses Rowen, Dublin (IE)

(73) Assignee: Centre for Commercialization of Regenerative Medicine, Toronto (CA)

( * ) Notice: Subject to any disclaimer, the term of this patent is extended or adjusted under 35 U.S.C. 154(b) by 136 days.

(21) Appl. No.: 17/416,345

(22) PCT Filed: Dec. 19, 2019

(86) PCT No.: PCT/CA2019/051863
§ 371 (c)(1),
(2) Date: Jun. 18, 2021

(87) PCT Pub. No.: WO2020/124245
PCT Pub. Date: Jun. 25, 2020

(65) Prior Publication Data
US 2022/0074531 A1    Mar. 10, 2022

Related U.S. Application Data

(60) Provisional application No. 62/782,776, filed on Dec. 20, 2018.

(51) Int. Cl.
*F16L 37/36*    (2006.01)
*A61M 39/26*    (2006.01)
(Continued)

(52) U.S. Cl.
CPC .............. *F16L 37/36* (2013.01); *A61M 39/18* (2013.01); *A61M 39/26* (2013.01); *B01L 3/567* (2013.01);
(Continued)

(58) Field of Classification Search
CPC ..... F16L 37/36; F16L 37/252; F16L 2201/44; A61M 39/26; A61M 39/16; A61M 39/18; B01L 3/567; B01L 2400/06
See application file for complete search history.

(56) References Cited

U.S. PATENT DOCUMENTS 2,203,922 A * 6/1940 Paisley .................... F16L 37/36
                                                                     251/148
4,256,106 A * 3/1981 Shoor .................... A61M 39/14
                                                                      604/905
4,334,551 A * 6/1982 Pfister .................... A61M 39/26
                                                                      604/905
(Continued)

FOREIGN PATENT DOCUMENTS

EP         2756863 A2 *  7/2014   ........ A61M 39/1011
WO   WO-2008094707 A1 *  8/2008   ............ A61M 39/14
WO   WO-2017102482 A1 *  6/2017   ......... B01D 15/1871

*Primary Examiner* — David Colon-Morales
(74) *Attorney, Agent, or Firm* — Bereskin & Parr LLP; Carmela De Luca

(57) ABSTRACT

Described here are systems and methods for a reusable, aseptic connector. A connector system provides aseptic fluid connection. The connector system has an inlet connector assembly having an inlet fluid passageway and an inlet valve configured to seal the inlet fluid passageway when in a disconnected state. The connector also has an outlet connector assembly having an outlet fluid passageway and an outlet valve configured to seal the outlet fluid passageway when in a disconnected state. The inlet valve is configured to couple to the outlet valve to form an aseptic fluid connection between the inlet and outlet fluid passageways when in a connected state.

18 Claims, 25 Drawing Sheets

1. Disconnected

(51) Int. Cl.
  *A61M 39/18* (2006.01)
  *B01L 3/00* (2006.01)
  *F16L 37/252* (2006.01)

(52) U.S. Cl.
  CPC ......... *F16L 37/252* (2013.01); *B01L 2400/06* (2013.01); *F16L 2201/44* (2013.01)

(56) References Cited

U.S. PATENT DOCUMENTS

| | | | | |
|---|---|---|---|---|
| 4,499,932 A * | 2/1985 | Perigo | ..................... | F16L 37/36 141/348 |
| 4,509,554 A * | 4/1985 | Failla | ..................... | F16L 29/04 137/614.04 |
| 4,921,013 A * | 5/1990 | Spalink | ..................... | F16L 37/36 137/614.01 |
| 5,492,147 A * | 2/1996 | Challender | ............. | F16L 37/28 604/905 |
| 5,884,648 A * | 3/1999 | Savage | ................... | F16L 37/36 137/614.04 |
| 6,077,259 A * | 6/2000 | Caizza | .................. | A61M 39/14 604/905 |
| 8,152,203 B2 * | 4/2012 | Olivier | ................... | F16L 37/36 604/905 |
| 8,746,278 B2 * | 6/2014 | Py | ........................... | F16L 37/36 251/340 |
| 8,899,267 B2 * | 12/2014 | Diodati | ................. | A61M 39/18 137/614.04 |
| 9,901,729 B2 * | 2/2018 | Vigna | ................... | F16L 37/367 |
| 10,864,364 B2 * | 12/2020 | Mack | ..................... | A61M 39/26 |
| 2010/0230950 A1 * | 9/2010 | Williams | ............. | A61M 39/18 285/38 |
| 2014/0290770 A1 * | 10/2014 | Py | ........................ | A61M 39/26 29/428 |

\* cited by examiner

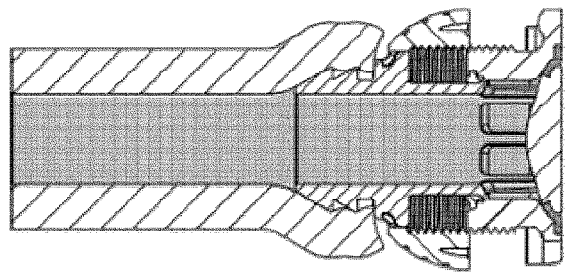 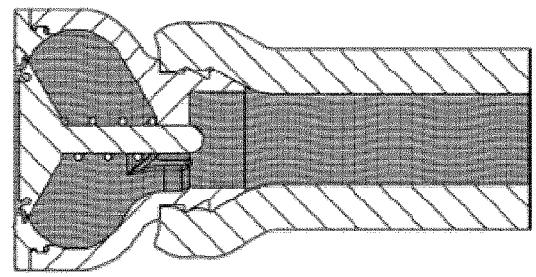
FIG. 21A
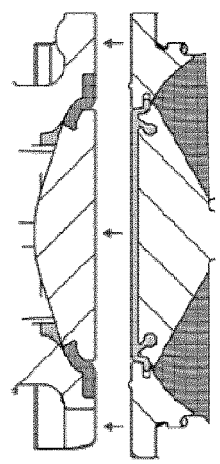 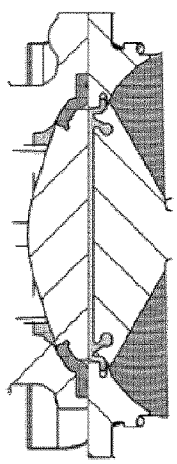 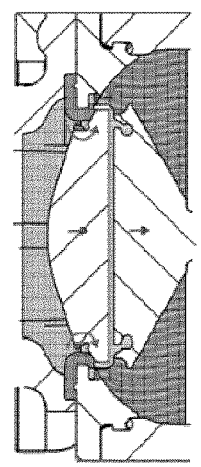
FIG. 21B        FIG. 21C        FIG. 21D
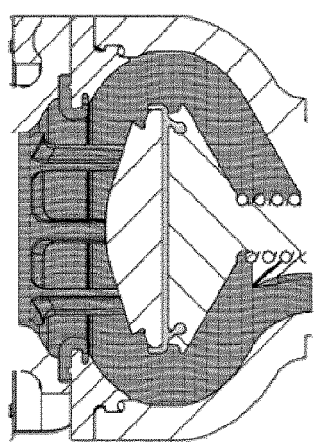 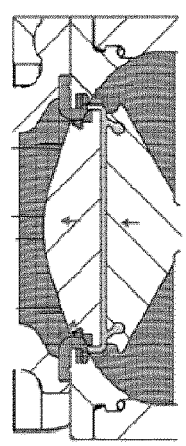 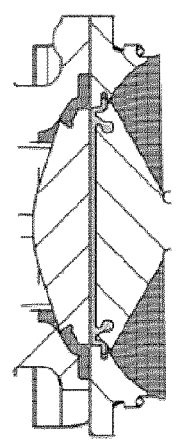
FIG. 21E        FIG. 21F        FIG. 21G 1. Disconnected 2. Connected, Closed 3. Connected, Opening,
   3mm valve lift 4. Connected, Fully Open,
   8mm valve lift 5. Connected, Closing,
   3mm valve lift

SYSTEMS AND METHODS FOR A REUSABLE, ASEPTIC CONNECTOR

CROSS-REFERENCE TO RELATED APPLICATIONS

This application claims the benefit of U.S. Provisional Patent Application Ser. No. 62/782,776, filed on Dec. 20, 2018, and entitled "SYSTEMS AND METHODS FOR A REUSABLE, ASEPTIC CONNECTOR," which is herein incorporated by reference in its entirety.

BACKGROUND

The present disclosure generally relates to fluid connectors. More specifically, the present disclosure relates to aseptic fluid connectors for cell and viral transport.

Within the cell therapy industry, maintaining an aseptic environment is of critical importance when transferring fluids containing cells. There are several single use aseptic connectors for small tubing on the market and multiuse large tubing connectors. These single use connectors are costly and can have limited utility since they may only be aseptically connected once.

Attempts have been made to produce a multi-use aseptic connector. However, such attempts have created connectors that often fail after only a few connection cycles and can leak residual fluid upon disconnection. Of further concern, these previous connectors often suffer from additional complications, such as having bulky or complex configurations that take a long time to connect and are limited large tubing.

Thus, there is a need for a multi-use connector that can maintain sterility of the fluid path before and after connection, with no fluid leakage after disconnection. Ideally, such a connector system could be quickly connected or disconnected without leakage, and be compatible with small and large tubing.

SUMMARY OF THE DISCLOSURE

The present disclosure addresses the aforementioned drawbacks by providing systems and methods for aseptic fluid connection using a connector system. The connector system described herein can be made compactly and be used to provide adjustable aseptic connection. Unlike many previous systems, the connector system of the present disclosure can repeatedly provide aseptic connection, and does not require additional disposable components. Advantageously, the connector system can be quickly connected and disconnected. Also, the connector system can provide a fluid path with no pinch points or narrowing that could cause disruption of cells.

In one aspect, the present disclosure provides a connector system for providing aseptic fluid connection. The connector system can comprise an inlet connector assembly having an inlet fluid passageway and an inlet valve configured to seal the inlet fluid passageway when in a disconnected state; and an outlet connector assembly having an outlet fluid passageway and an outlet valve configured to seal the outlet fluid passageway when in a disconnected state, wherein the inlet valve is configured to couple to the outlet valve and move within the inlet fluid passageway or outlet fluid passageway to form an aseptic fluid connection between the inlet and outlet fluid passageways when in a connected state.

In another aspect, the present disclosure provides a connector system for providing aseptic fluid connection. The connector system can comprise an inlet connector assembly having an inlet fluid passageway and an inlet valve configured to seal the inlet fluid passageway when in a disconnected state; and an outlet connector assembly having an outlet fluid passageway and an outlet valve configured to seal the outlet fluid passageway when in a disconnected state, wherein the inlet valve is configured to couple to the outlet valve to form an aseptic fluid connection between the inlet fluid passageway and outlet fluid passageway when in a connected state; and wherein the inlet valve comprises an inlet valve seal that has a rim configured to undergo a change in orientation when the connector assembly changes state.

In one aspect, the present disclosure provides a method for providing aseptic fluid connection. The method can comprise providing an inlet connector assembly having an inlet fluid passageway and an inlet valve configured to seal the inlet fluid passageway when in a disconnected state; providing an outlet connector assembly having an outlet fluid passageway and an outlet valve configured to seal the outlet fluid passageway when in a disconnected state; coupling the inlet valve to the outlet valve; and moving the coupled inlet valve and outlet valve within the inlet fluid passageway or outlet fluid passageway to form an aseptic fluid connection between the inlet and outlet fluid passageways when in a connected state.

In another aspect, the present disclosure provides a method for providing aseptic fluid connection. The method can comprise providing an inlet connector having an inlet fluid passageway and an inlet valve configured to seal the inlet fluid passageway when in a disconnected state; providing an outlet connector having an outlet fluid passageway and an outlet valve configured to seal the outlet fluid passageway when in a disconnected state; and coupling the inlet valve to the outlet valve to form an aseptic fluid connection between the inlet fluid passageway and outlet fluid passageway, wherein the inlet valve comprises an inlet valve seal that has a rim configured to undergo a change in orientation when the connector assembly changes state.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

BRIEF DESCRIPTION OF THE DRAWINGS

FIGS. 21A-G are schematic illustrations of the stages of movement of the inlet and outlet valves as the connector system transitions from a disconnected, closed state (FIG. 21A) to a connected, open state (FIG. 21E), and then back to a connected, closed state (FIG. 21G).

DETAILED DESCRIPTION

Described here are systems and methods for aseptic fluid connection. The connector system described herein can provide reusable, aseptic connection. The connector system can be quickly connected or disconnected, often within less than 10 seconds, and can require no single use components. In order to achieve this functionality, the connector system can employ a unique valve configuration. In this configuration, the two valves that ensure no individual leakage of the connectors when in a disconnected state, couple together in a connected state. This configuration can prevent the contaminated portions of the valves to be exposed to the fluid passing through the connector system by remaining sealed from the fluid, while the coupled valves move to provide fluid connection between the connectors.

The systems and methods described in the present disclosure are applicable to any process that benefits from maintaining an aseptic fluid connection. Such processes can include fluid transfer within the medical field, such as the transport of solutions containing cells. As another example, the processes can include fluid transfer within the cell and tissue culturing fields, virus and protein producing fields, and any other related fields where cell-containing fluids, growth media, factors, and so on, may need to be transferred between containers.

Figure 1:
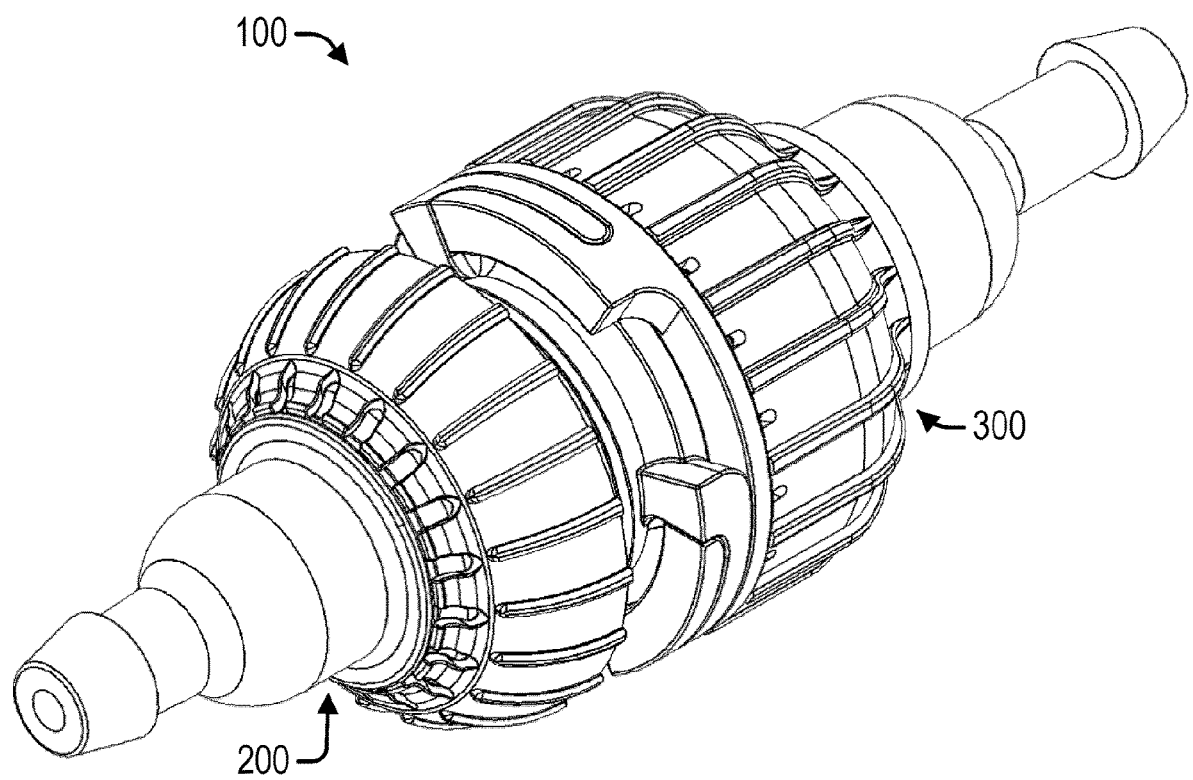
FIG. 1 is an isometric view of an illustration of a connector system in a connected, closed state.
Figure 2:
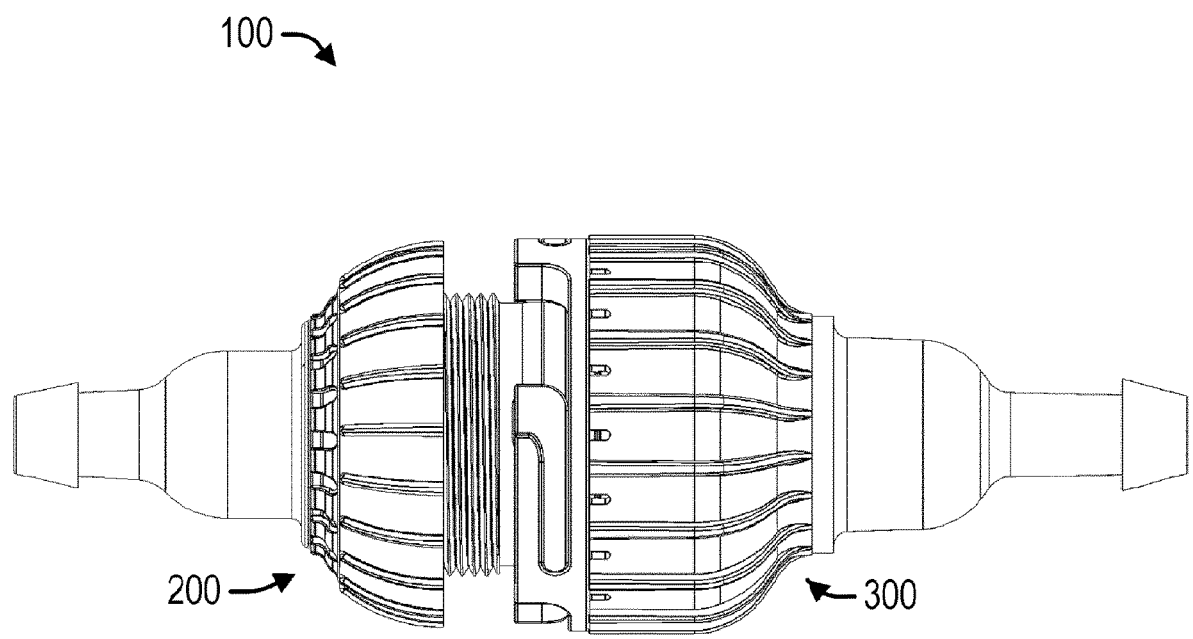
FIG. 2 is a side view of an illustration of a connector system in a connected, closed state.
Figure 3:
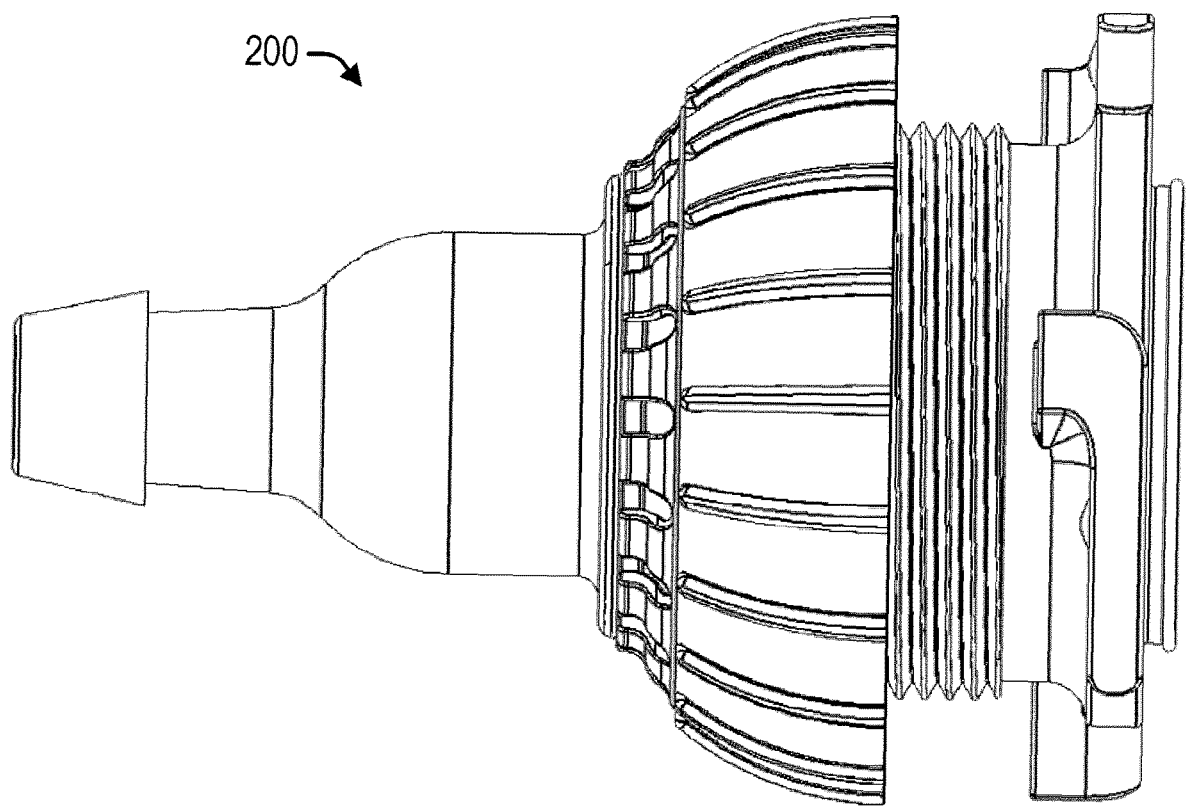
FIG. 3 is a side view of an illustration of an outlet connector assembly in a disconnected, closed state.
Figure 4A:
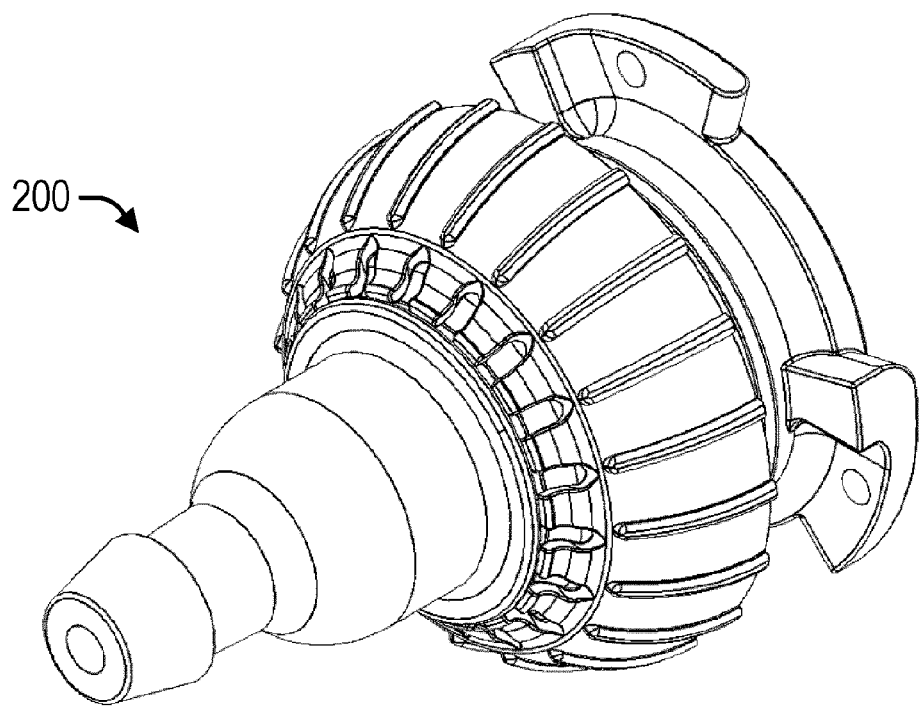
FIG. 4A is a front isometric view of an illustration of the outlet connector assembly in a disconnected, closed state.
Figure 4B:
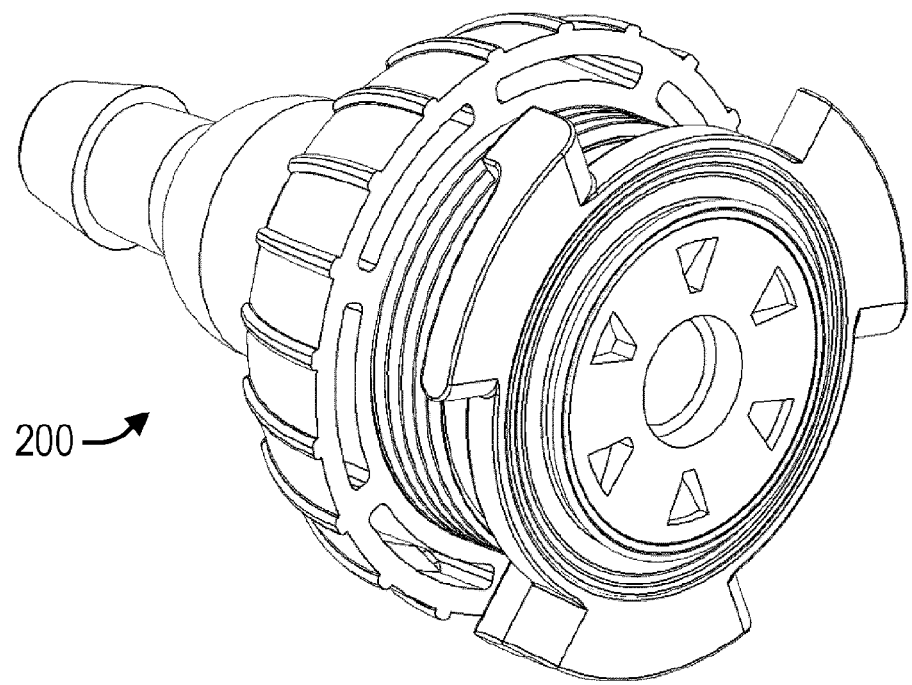
FIG. 4B is a back isometric view of an illustration of the outlet connector assembly in a disconnected, closed state.
Figure 5A:
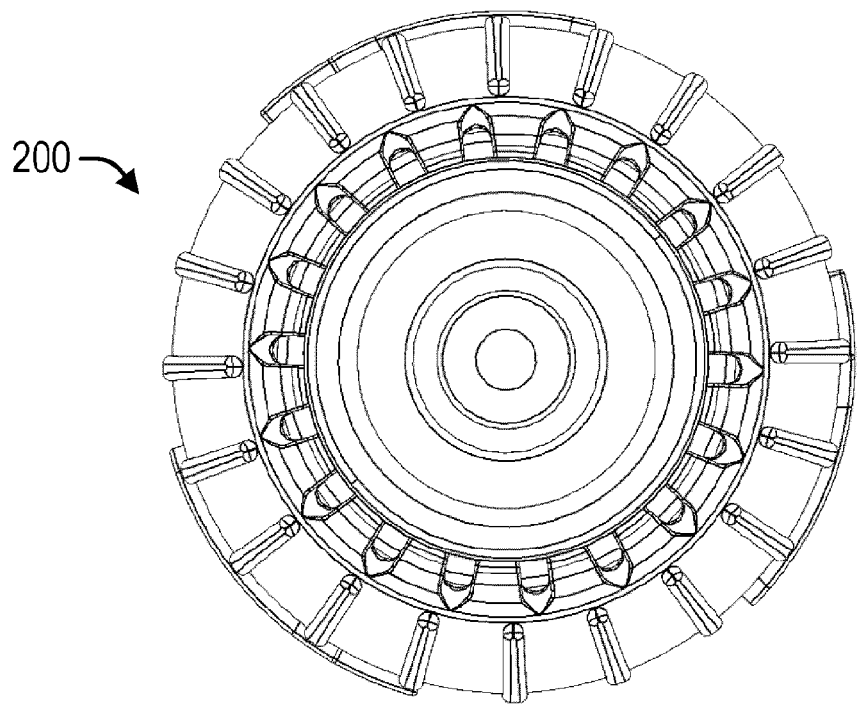
FIG. 5A is a front view of an illustration of the outlet connector assembly in a disconnected, closed state.
Figure 5B:
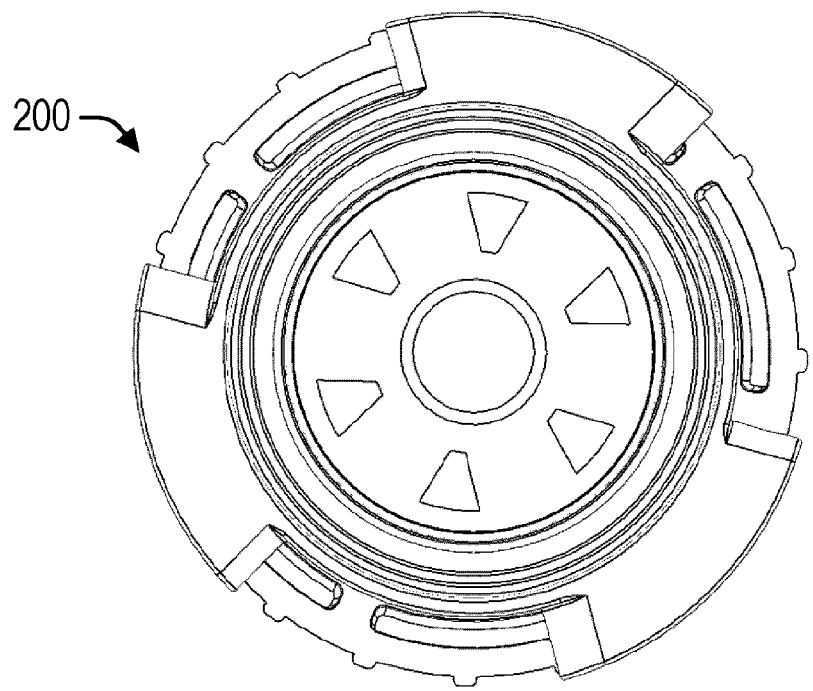
FIG. 5B is a back view of an illustration of the outlet connector assembly in a disconnected, closed state.
Figure 6:
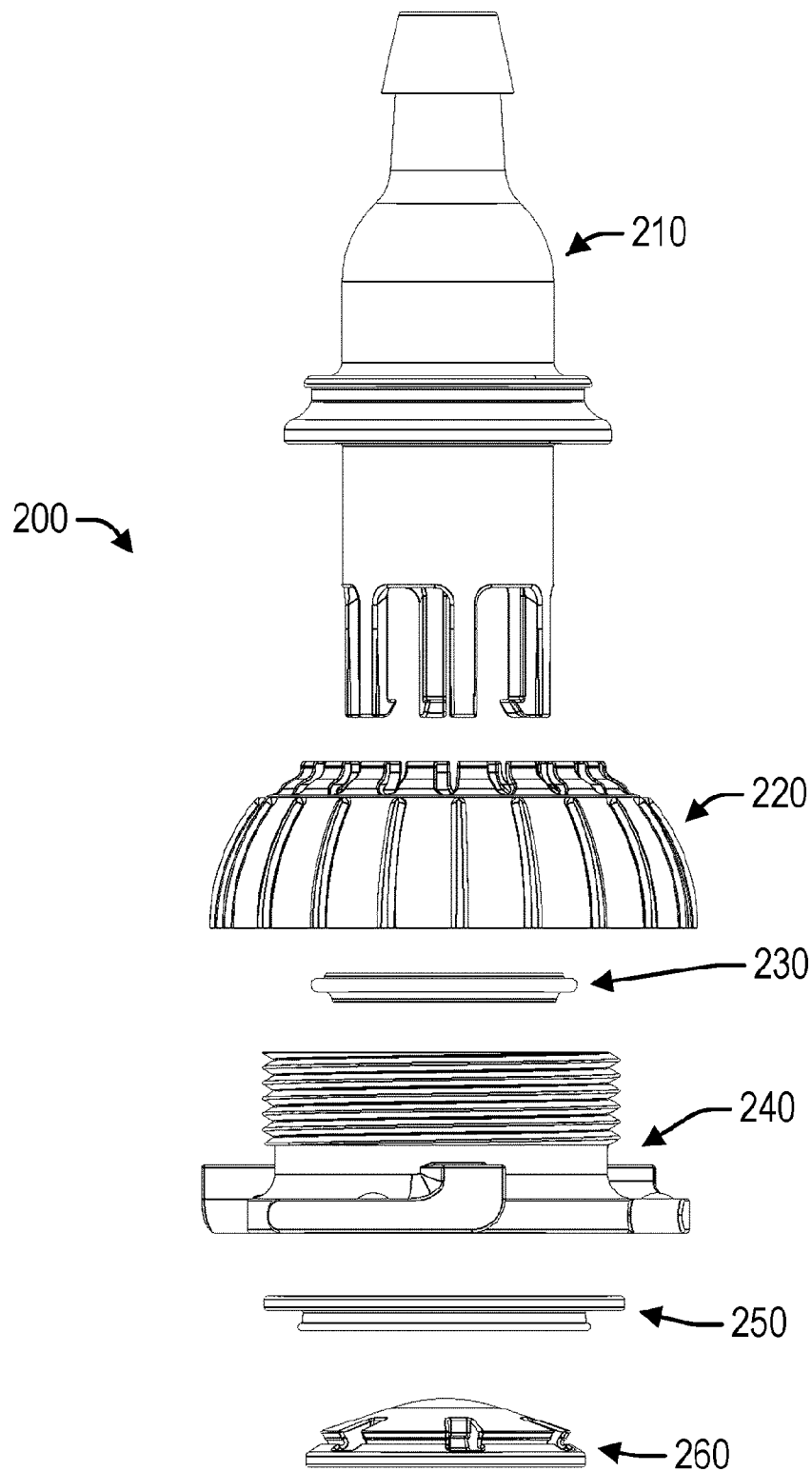
FIG. 6 is an exploded view of an illustration of the outlet connector assembly.

Referring to FIGS. 1-2, an embodiment of the connector system 100 is depicted in a connected, closed state. The connector system may generally comprise an outlet connector assembly 200 and an inlet connector assembly 300. The connector system may exist in either a connected state or disconnected state. When the outlet connector and the inlet connector are coupled in a connected state, the connector system may exist in closed state or an open state. The open state may vary in degree from being only partially open to fully open. In this manner, the connector system 100 may provide aseptic fluid connection between the outlet connector assembly 200 and an inlet connector assembly 300, when in an open state.

Referring now to FIGS. 3-6, one embodiment of the outlet connector assembly 200 is shown in a disconnected, closed state. As shown in the exploded depiction of FIG. 6, the outlet connector assembly 200 may include an outlet tube 210, a thumb wheel 220, a sliding seal 230, an outlet connector 240, an outlet valve seal 250, and an outlet valve 260. These components combine to provide the unique functionality of the outlet connector assembly 200. Such functionality may include allowing the outlet connector assembly 200 to provide aseptic fluid connection when in a connected, open state, and seal the fluid connection when in a closed state.

Figure 7:
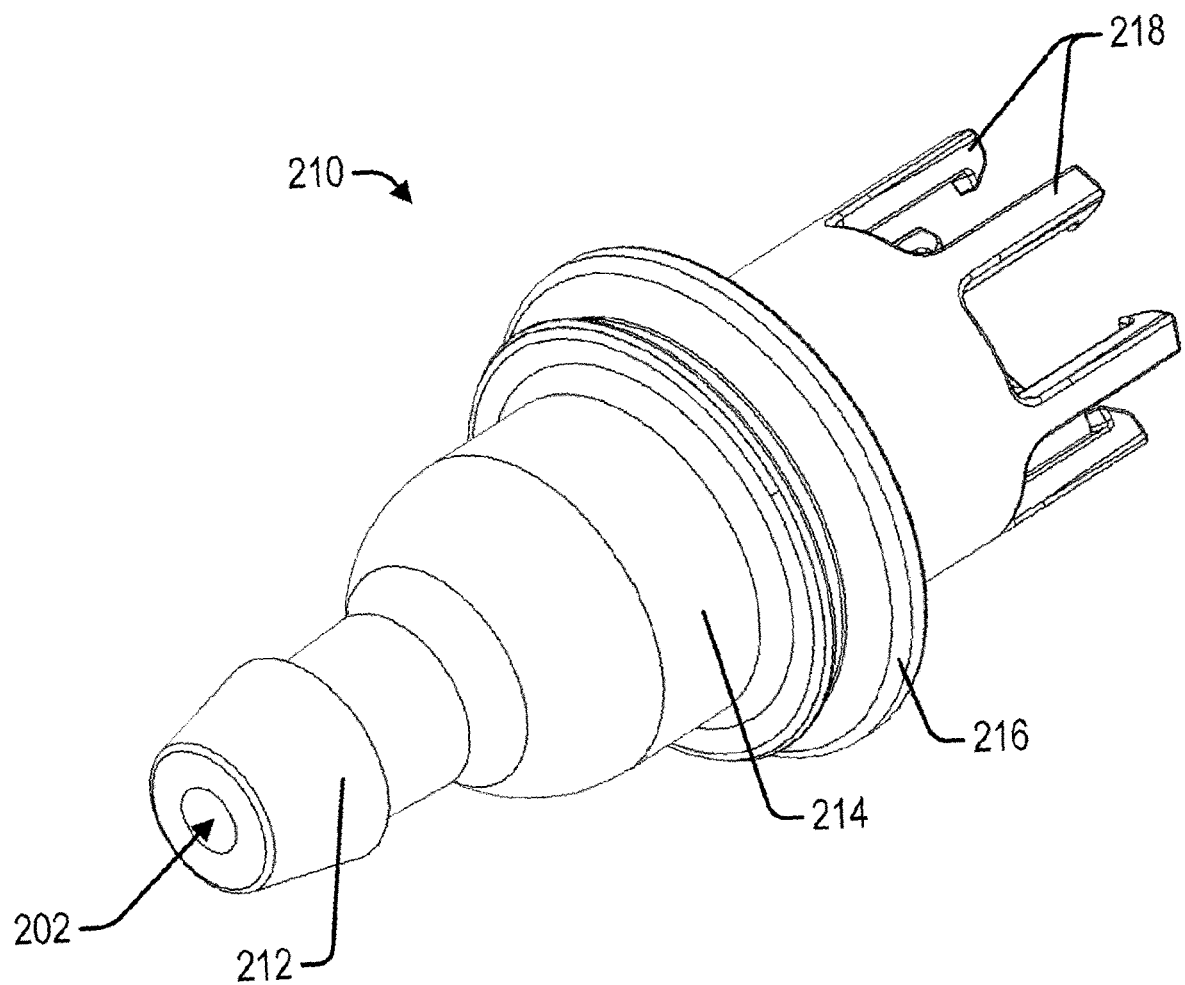
FIG. 7 is an isometric view of an illustration of an outlet tube of the outlet connector assembly.

FIG. 7 depicts the outlet tube 210 of the outlet connector assembly 200. The outlet tube may be formed of a body 214. An outlet tubing connector 212, a snap rim 216, and a plurality of snap teeth 218 may be integrated with the body 214. These components may generally define an outlet fluid passageway 202 which may extend through the outlet tube 210. The outlet tubing connector 214 may function to provide a fitting to connect the outlet fluid passageway 202 with an external tube or conduit. The snap rim 216 may function to connect the outlet tube 210 to the thumb wheel 220. The snap teeth 218 may function to connect the outlet tube 210 to the outlet valve 260. Although snap fittings are used in this embodiment, one of skill in the art will recognize that other means of achieving this functionality may be used.

Figure 8:
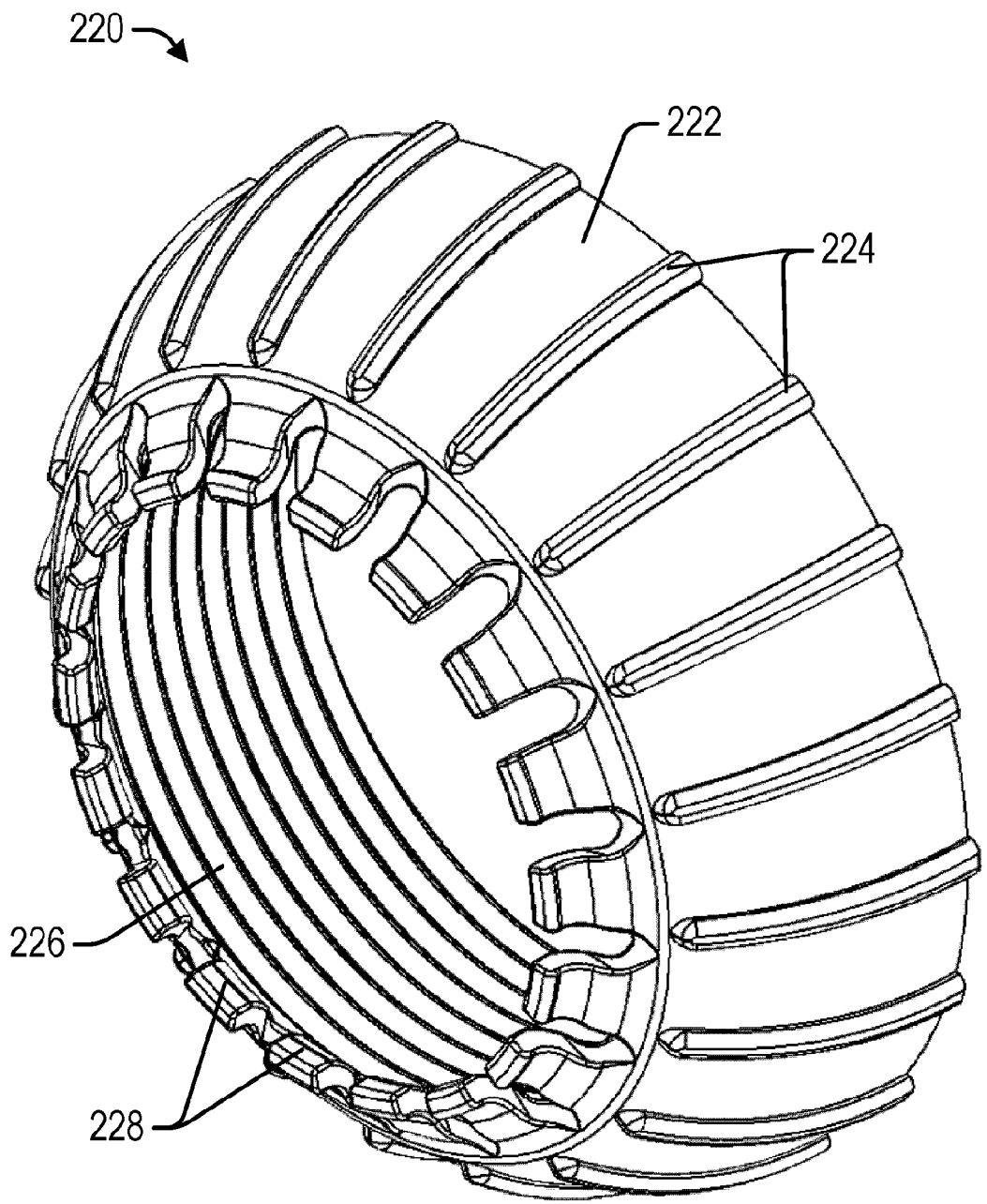
FIG. 8 is an isometric view of an illustration of a thumb wheel of the outlet connector assembly.

FIG. 8 depicts the thumb wheel 220 of the outlet connector assembly 200. The thumbwheel 220 may be formed of a body 222. A plurality of grip elements 224, internal threads 226, and a plurality of snap teeth 228 may be integrated with the body 222. The snap teeth 228 may be configured to couple to the snap rim 216, thereby integrating the thumb wheel 220 and the outlet tube 210. The plurality of grip elements 224 may function to allow a user to easily rotate the thumb wheel by reducing the risk of slippage.

Figure 9:
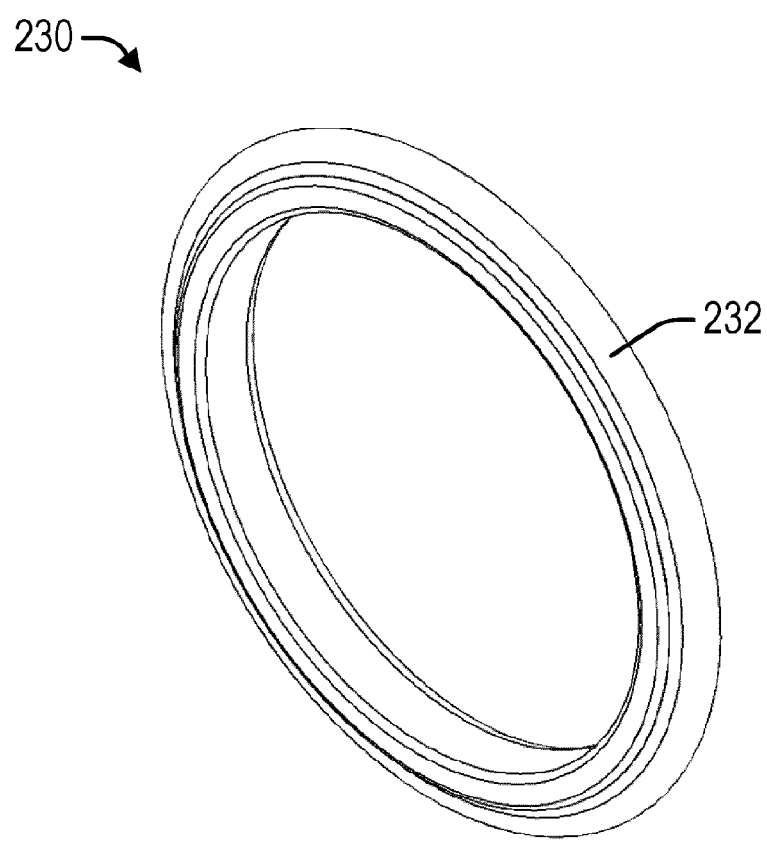
FIG. 9 is an isometric view of an illustration of a sliding seal of the outlet connector assembly.

FIG. 9 depicts a sliding seal 230 which may be formed of an annular body 232. The sliding seal 230 may be a pressure activated sliding seal. The annular body 232 may be configured to couple to the outlet connector 240. In this manner, as the integrated outlet tube 210 and thumbwheel 220 may move relative to the outlet connector 240 while the sliding seal 230 maintains a seal with the outlet tube body 214, thereby preventing fluid leakage.

Figure 10:
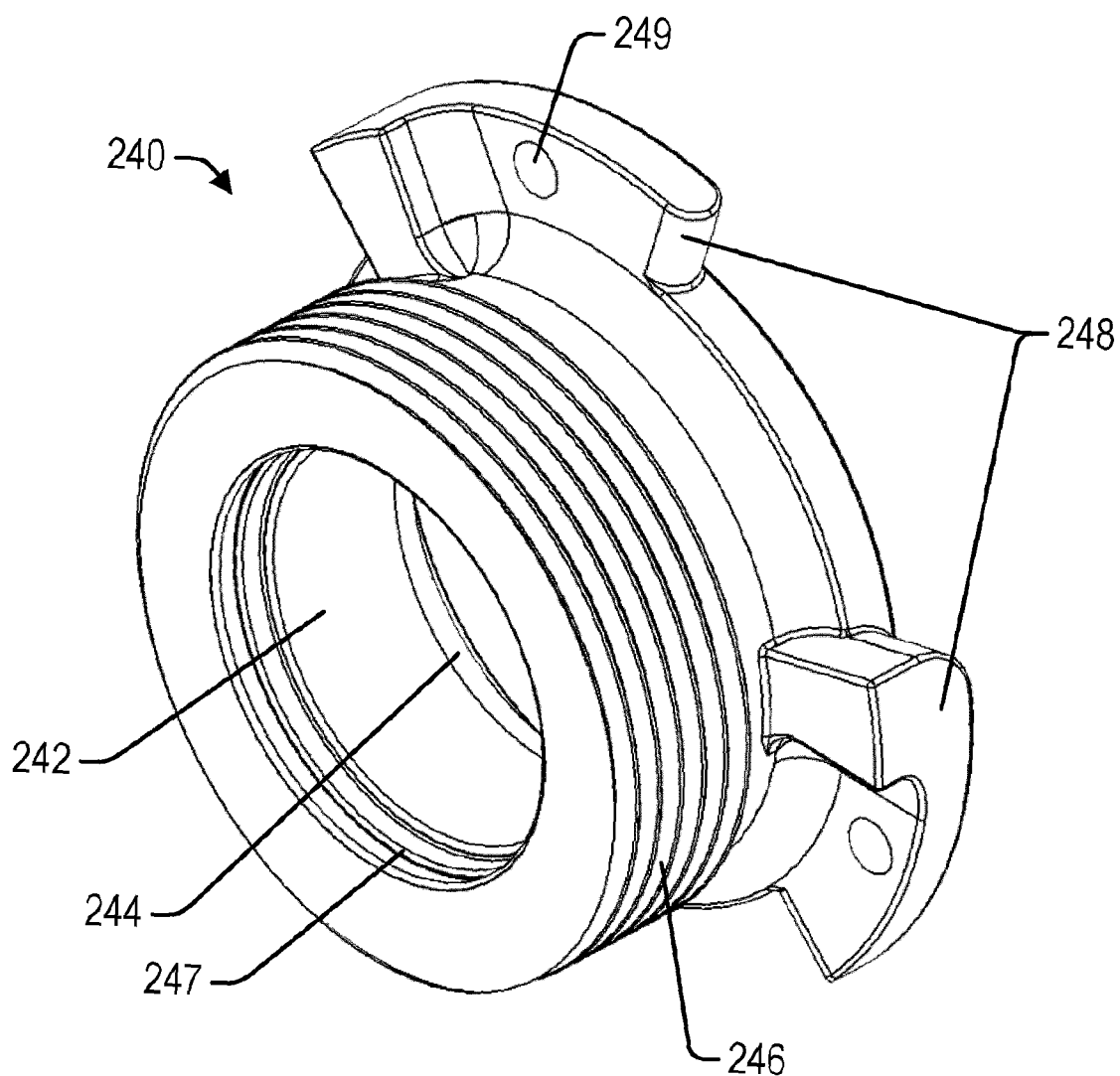
FIG. 10 is an isometric view of an illustration of an outlet connector of the outlet connector assembly.

FIG. 10 depicts an outlet connector 240 of the outlet connector assembly 200. The outlet connector 240 may be formed of a body 242. External threads 246, internal protrusions 247, and a plurality of mating components 248 may be integrated with this body 242. As will be described below, the mating components 248 allow for the outlet connector 240 to be mated, or otherwise coupled, to the inlet connector 310. The body 242 also may define a portion 244 configured to receive the outlet valve 260. The internal protrusions 247 may be configured to integrate the sliding seal 230 to the outlet connector 240. The external threads 246 may be configured to interact with the internal threads 226 of the thumbwheel 220 to move the integrated outlet tube 210 and thumbwheel 220 relative to the outlet connector 240 as a user rotates the thumbwheel 220. Consequently, the thumbwheel 220 may be sized to receive the outlet connector 240.

The external threads 246 of the outlet connector 240 may have a thread angle, helix angle, and pitch that is compatible with the internal threads 226 of the thumbwheel 220. Although the present embodiment focuses on a rotating mechanism to provide the adjustable motion, one of skill in the art will recognize that other means of achieving this functionality may be used. For instance, the connector system may use a simple linear sliding component instead of the threaded thumb wheel 220.

Figure 11A:
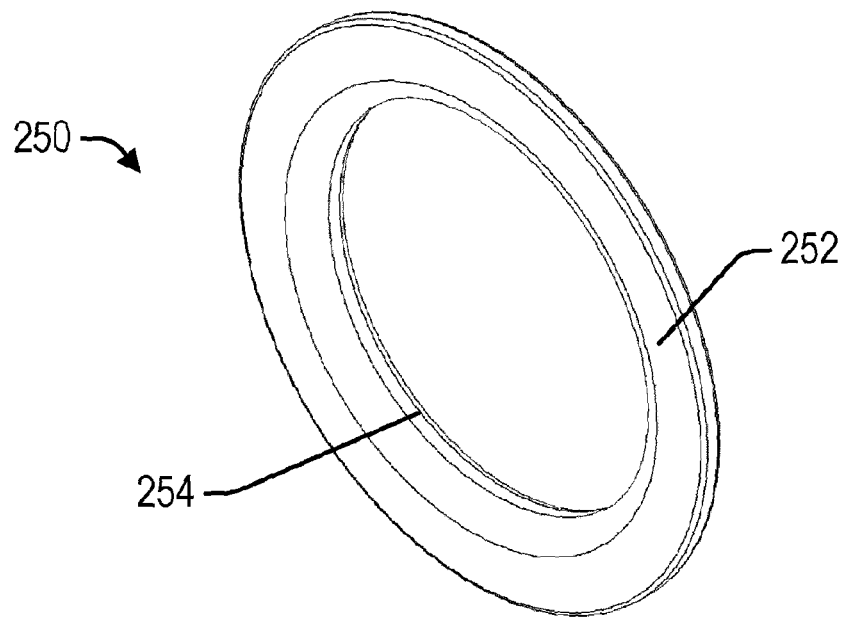
FIG. 11A is a front isometric view of an illustration of an outlet valve seal of the outlet connector assembly.
Figure 11B:
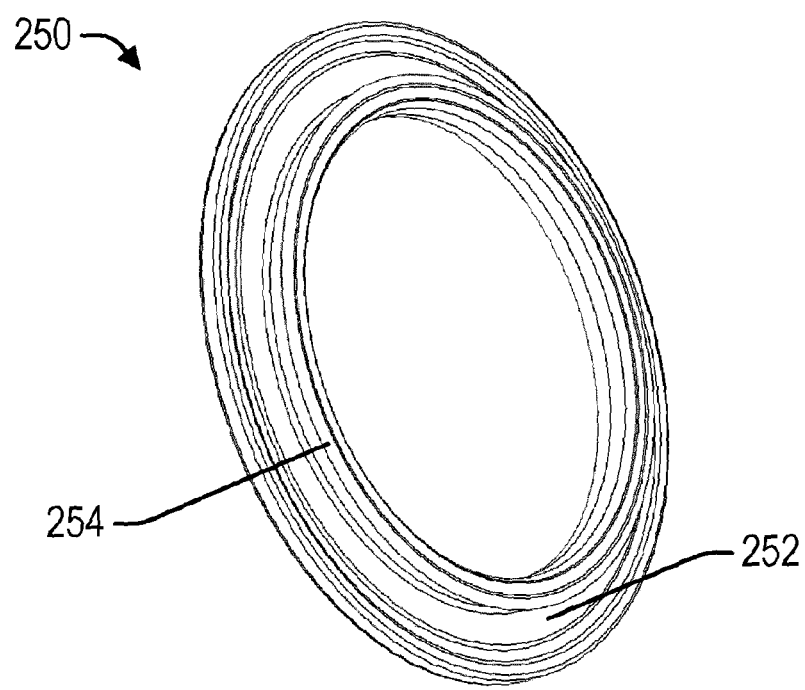
FIG. 11B is a back isometric view of an illustration of an outlet valve seal of the outlet connector assembly.

FIGS. 11A-B depict an outlet valve seal 250 of the outlet connector assembly 200. The outlet valve seal 250 may include an annular body 252 and a sealing rim 254. The outlet valve seal 250 may be configured to seal the outlet fluid passageway 202 when pressure is applied by the outlet valve 260. When in a closed state, the outlet valve seal 250 may be tightly positioned between the outlet valve 260 and the outlet connector portion 244.

Figure 12A:
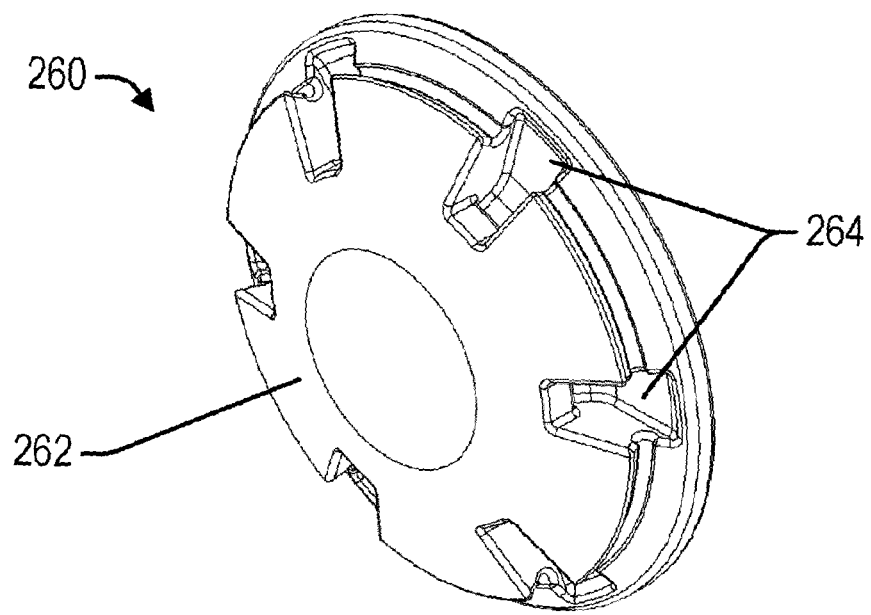
FIG. 12A is a front isometric view of an illustration of an outlet valve of the outlet connector assembly.
Figure 12B:
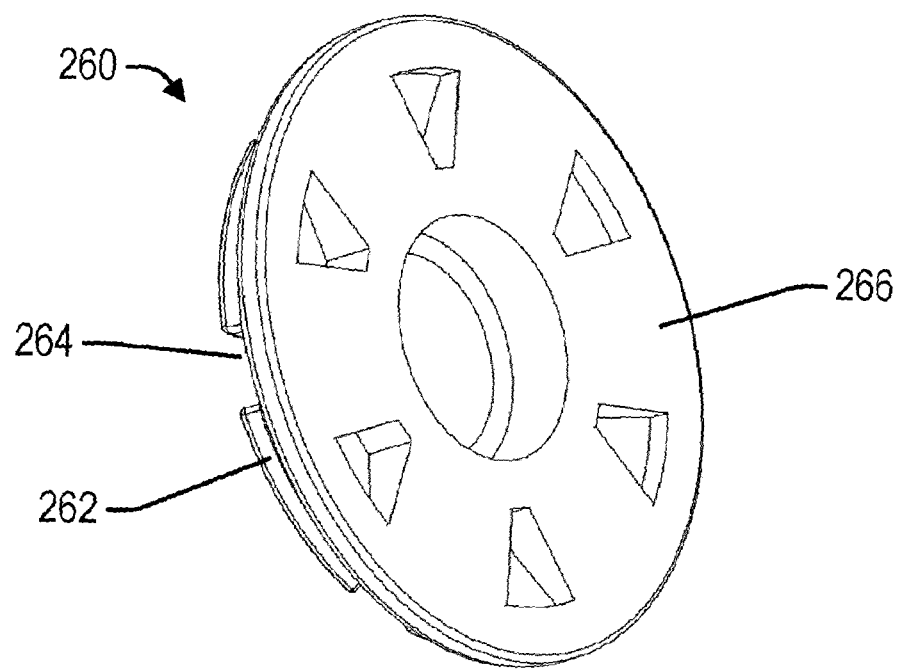
FIG. 12B is a back isometric view of an illustration of an outlet valve of the outlet connector assembly.
Figure 13:
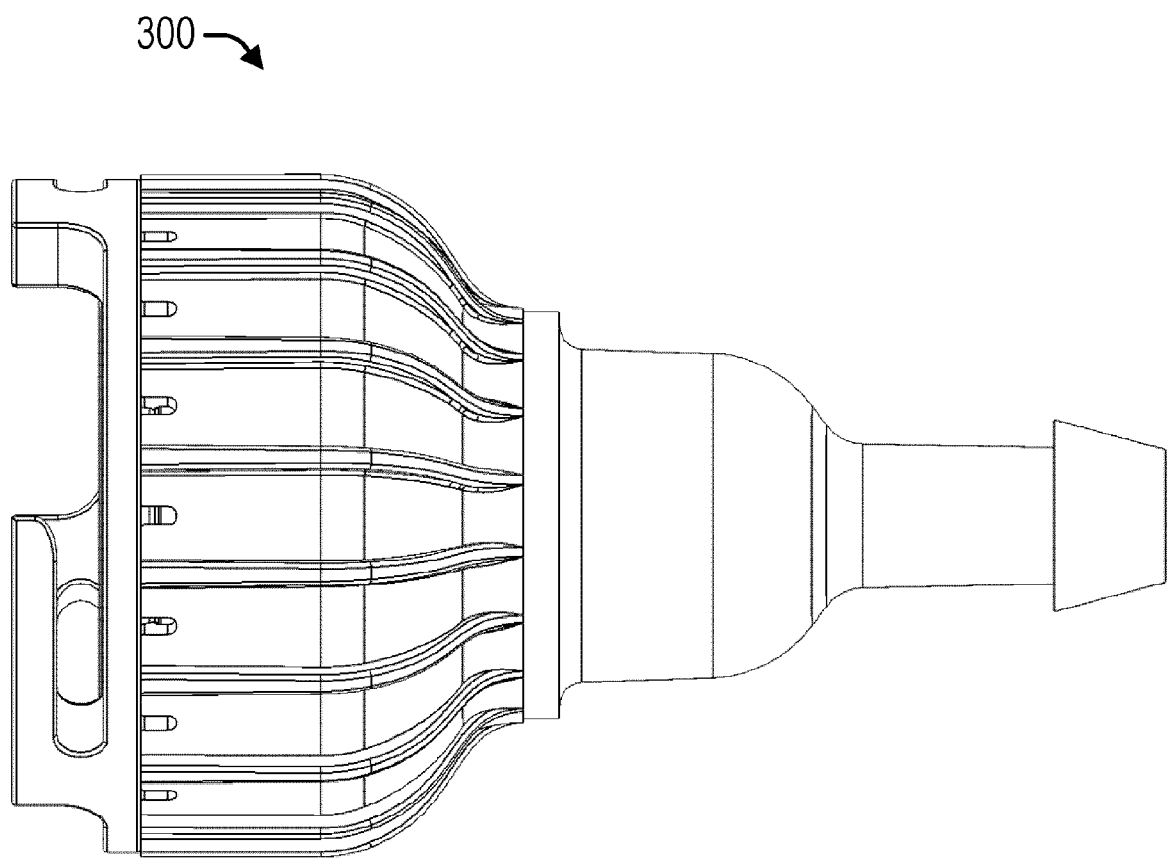
FIG. 13 is a side view of an illustration of an inlet connector assembly in a disconnected, closed state.
Figure 14A:
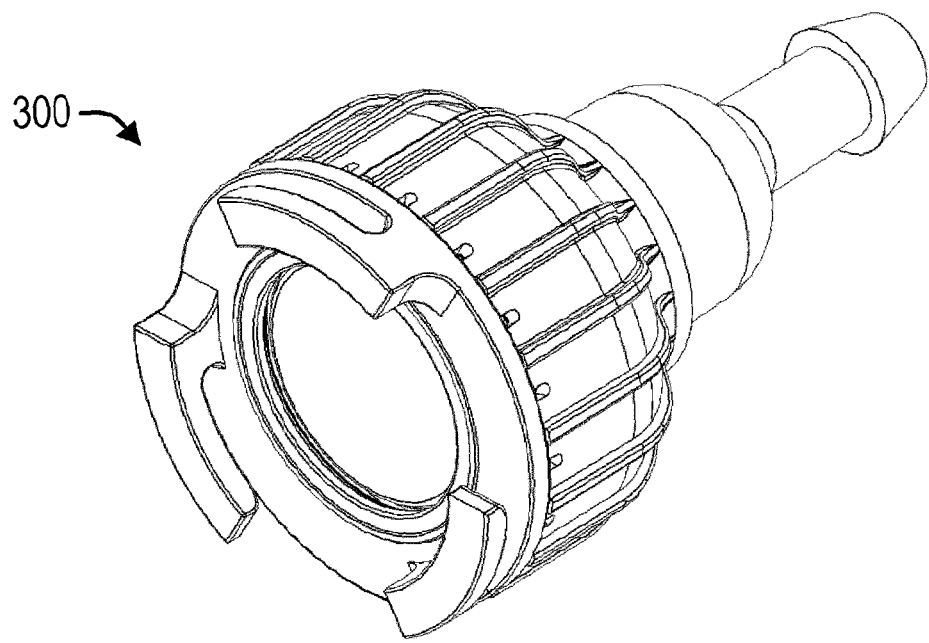
FIG. 14A is a front isometric view of an illustration of the inlet connector assembly in a disconnected, closed state.
Figure 14B:
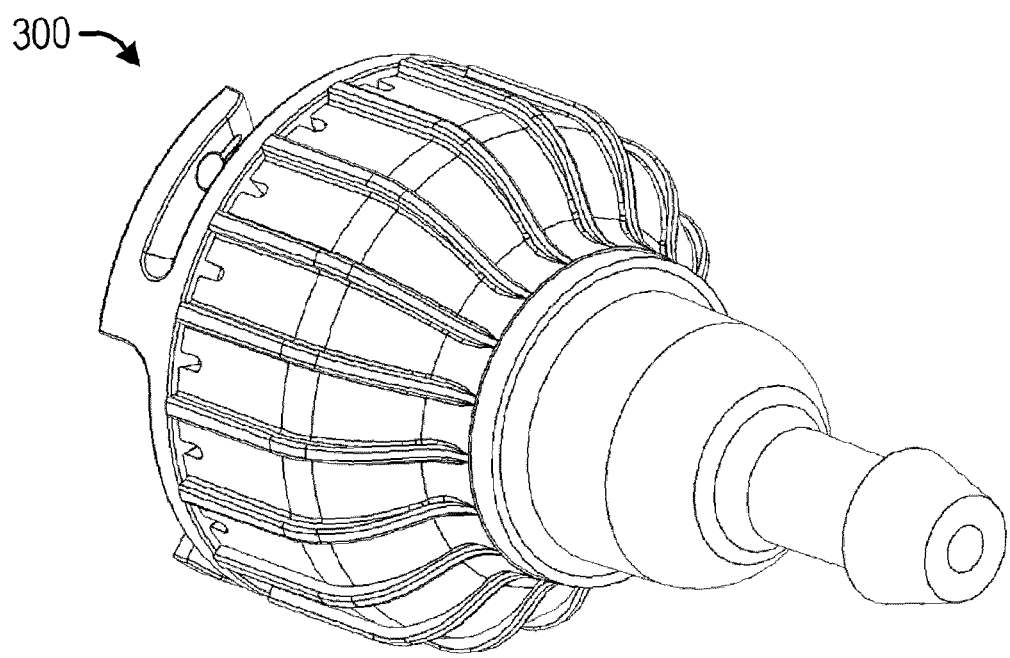
FIG. 14B is a back isometric view of an illustration of the inlet connector assembly in a disconnected, closed state.
Figure 15A:
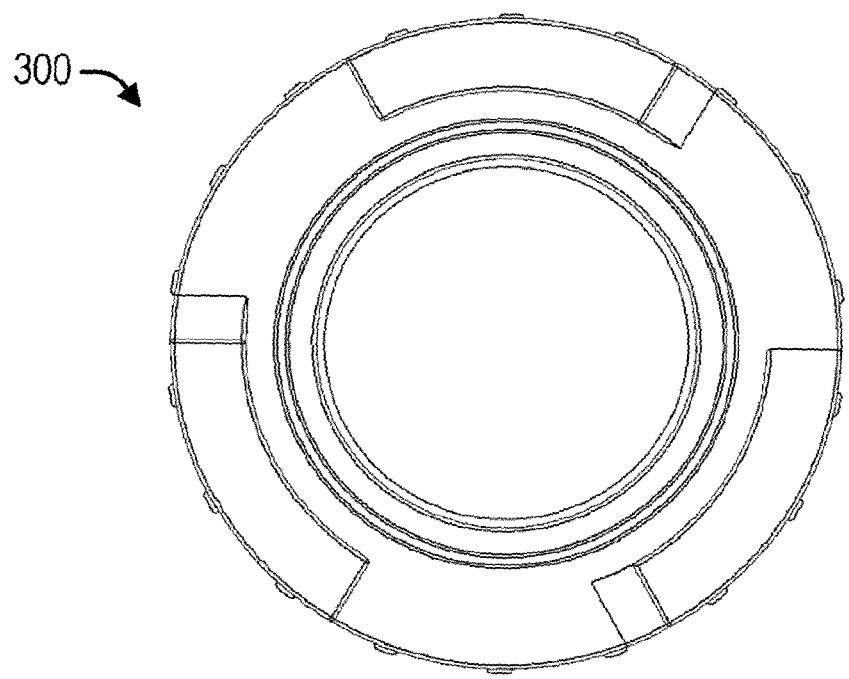
FIG. 15A is a front view of an illustration of the inlet connector assembly in a disconnected, closed state.
Figure 15B:
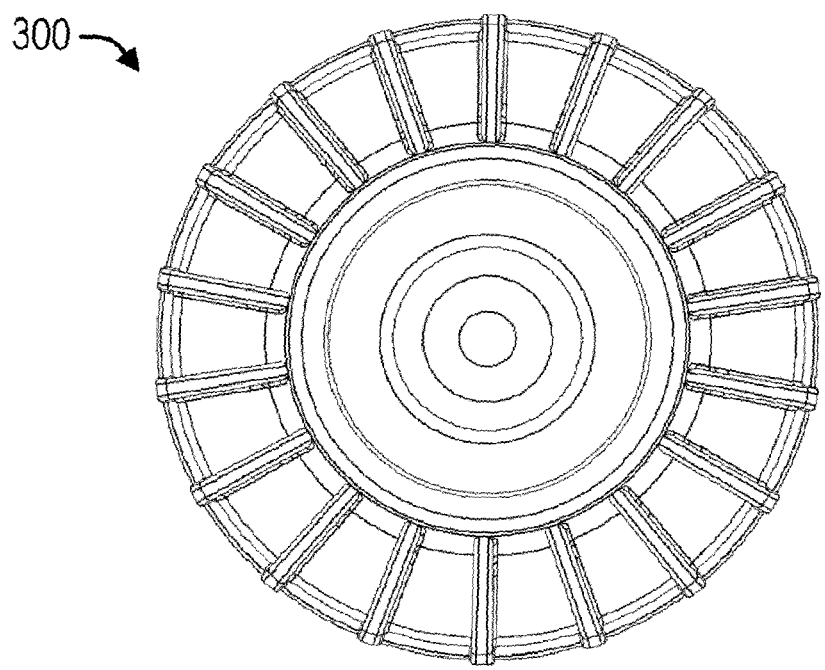
FIG. 15B is a back view of an illustration of the inlet connector assembly in a disconnected, closed state.
Figure 16:
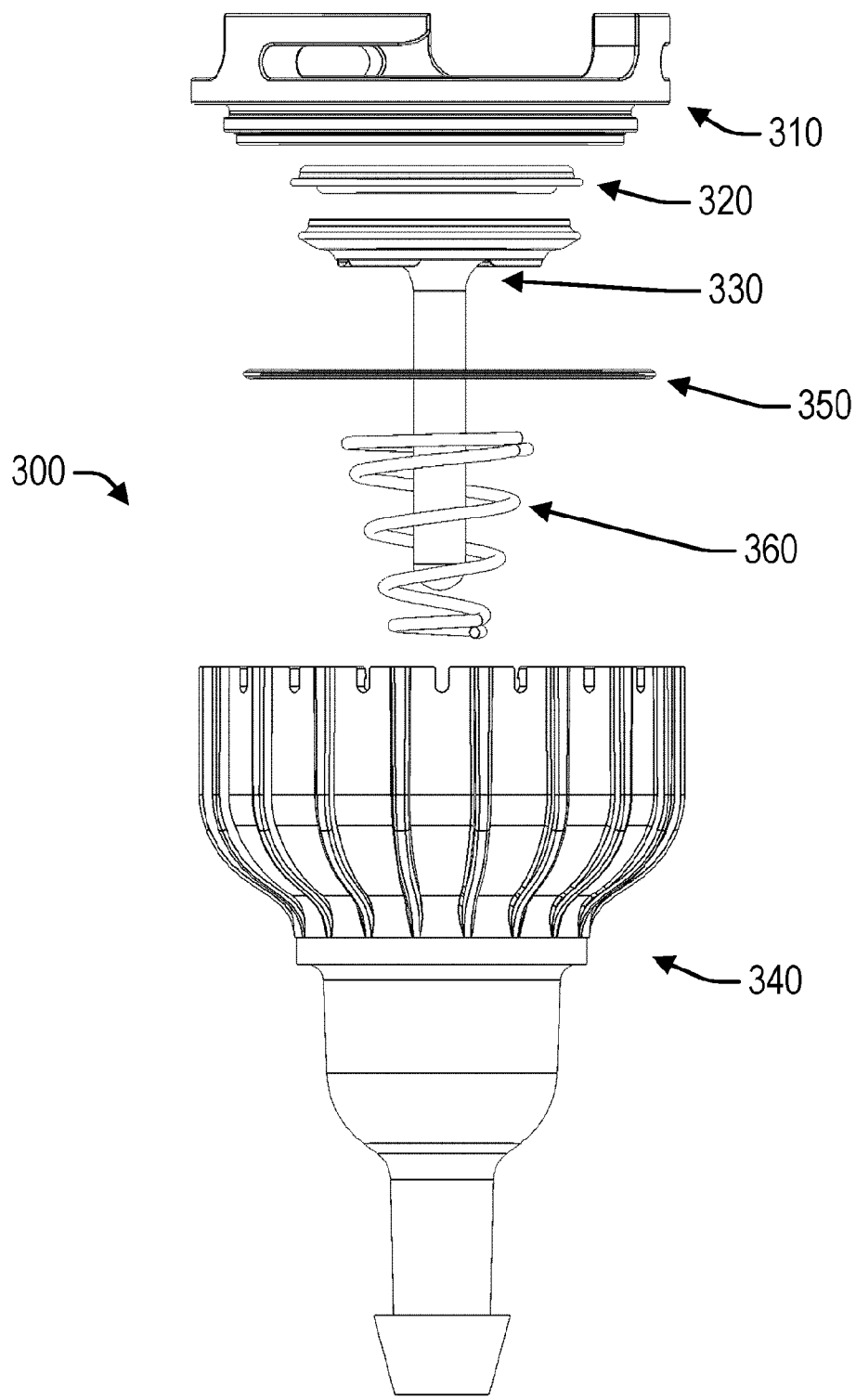
FIG. 16 is an exploded view of an illustration of the inlet connector assembly.

FIGS. 12A-B depict an outlet valve 260 of the outlet connector assembly 200. The outlet valve 260 may have a body 262. The body 262 may define a plurality of snap recesses 264 and an external portion 266. The external portion 266 may include the entire portion of the outlet valve 260 that is exposed to the surrounding environment when the outlet connector assembly 200 is in a disconnected, closed state. To maintain an aseptic connection, the external portion 266 will generally be sealed from contact with any fluid passageway when the connector system 100 is in the connected, open state. The snap recesses 264 may couple with the outlet tube snap teeth to connect the outlet tube 210 to the outlet valve 260. Consequently, the outlet valve 260 may be indirectly connected to the thumbwheel 220. Thus, as the thumbwheel 220 rotates and moves linearly, the outlet valve 260 may move in tandem. This integration may allow the outlet connector assembly 200 to change from an open to a closed state, and vice versa. This arrangement may also allow a user to control the degree to which the outlet connector assembly 200 is open, and thus, to control the flowrate through the connector system.

Referring now to FIGS. 13-16, one embodiment of the inlet connector assembly 300 is shown in a disconnected, closed state. As shown in the exploded depiction of FIG. 16, the inlet connector assembly 300 may include an inlet connector 310, an inlet valve seal 320, an inlet valve 330, an inlet plenum 340, a gasket 350, and a spring 360. These components combine to provide the unique functionality of the inlet connector assembly 300. Such functionality may include allowing the inlet connector assembly 300 to provide aseptic fluid connection when in a connected, open state, and seal the fluid connection when in a closed state.

Figure 17A:
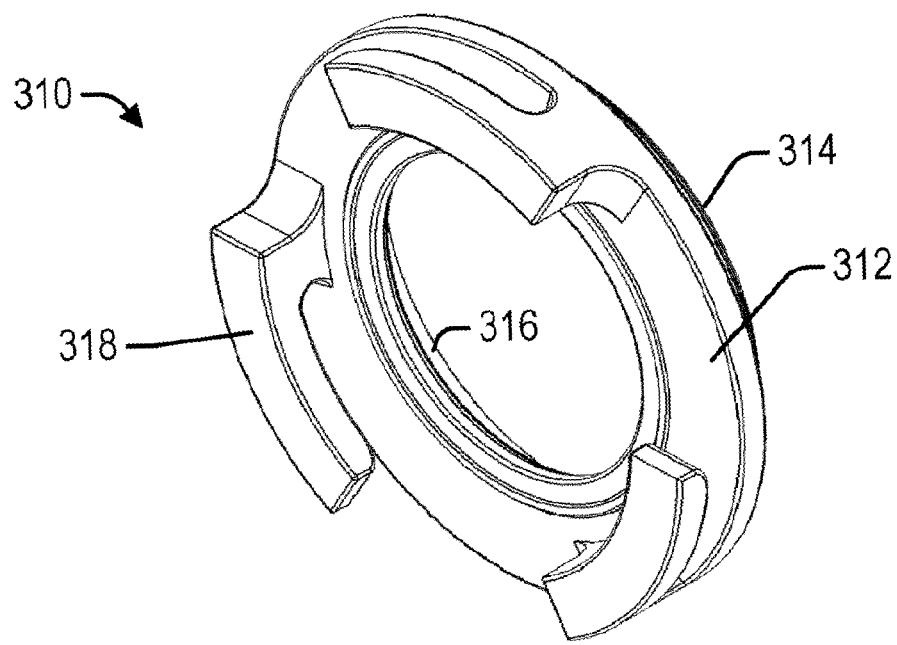
FIG. 17A is a front isometric view of an illustration of an inlet connector of the inlet connector assembly.
Figure 17B:
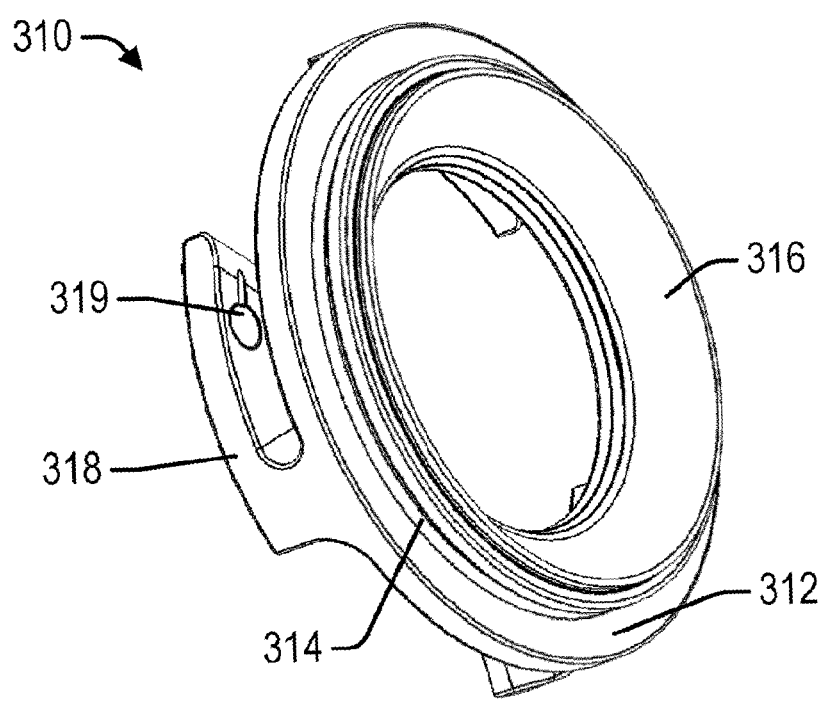
FIG. 17 B is a back isometric view of an illustration of an inlet connector of the inlet connector assembly.

FIGS. 17A-B depicts an inlet connector 310 of the inlet connector assembly 300. The inlet connector 310 may be generally formed of a body 312. This body 312 may define a recessed rim 314 configured to couple the inlet connector 310 to the inlet plenum 340. The body may also define a portion 316 for receiving the inlet valve 330. A plurality of mating components 318 may be integrated with the body 312.

The plurality of inlet connector mating components 318 may be configured to connect to the outlet connector mating components 248. In this manner, the inlet connector assembly 300 may connect with the outlet connector assembly 200 to form a connected state. Although interlocking arms are depicted as the mating components 248, 318, clips, threads, magnets, adhesives, as well as other known connector means may be used as the mating components 248, 318. The mating components 248, 318 may have locking features configured to lock the inlet connector 310 and outlet connector 240 together when fully connected. In the depicted embodiment, the outlet connector mating components 240 may comprise dimples 249 configured to lock into indentations 319 on the inlet connector mating components 318. Such locking features may prevent the mating components 248, 318 from spreading, thereby making it difficult for a user to accidentally disconnect the connector system when in a connected, open state, which would compromise sterility and spill fluid.

Figure 18A:
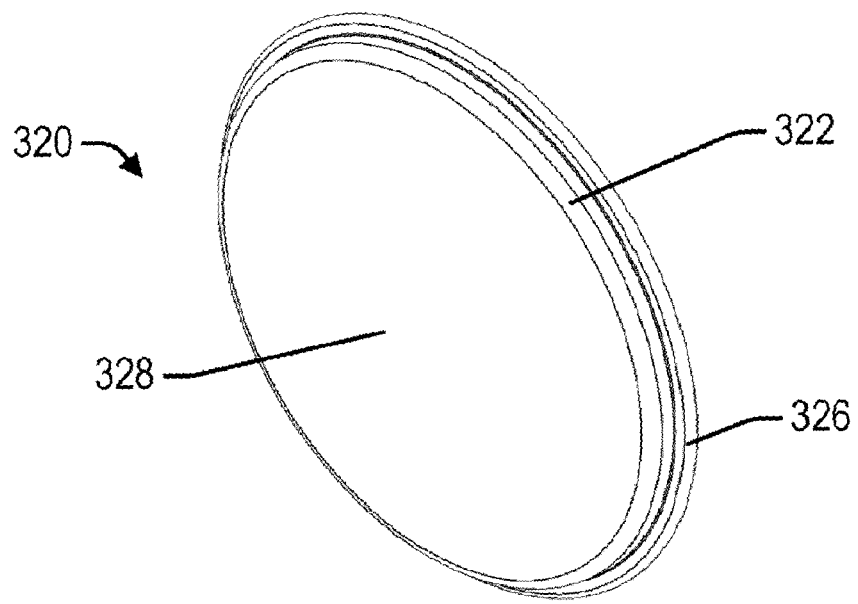
FIG. 18A is a front isometric view of an illustration of an inlet valve seal of the inlet connector assembly.
Figure 18B:
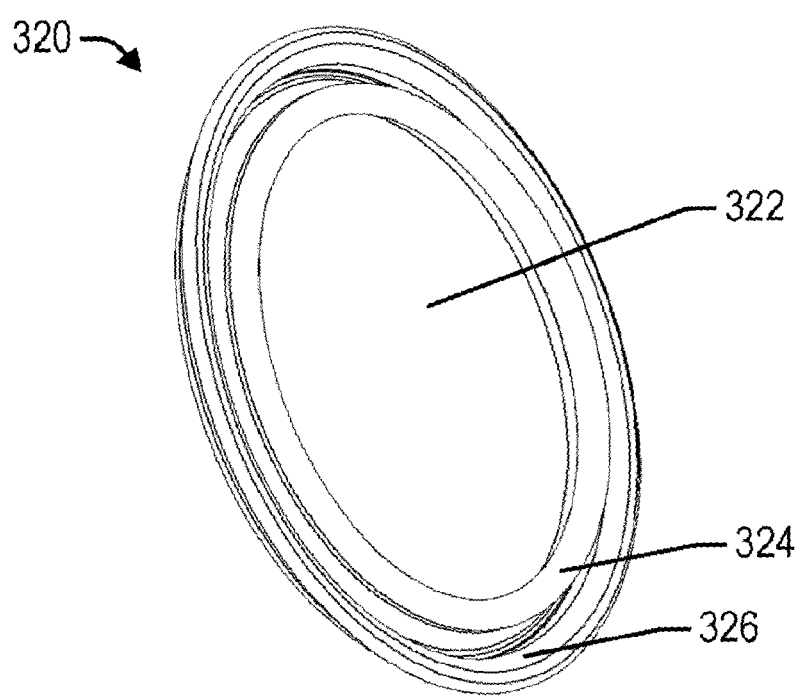
FIG. 18B is a back isometric view of an illustration of an inlet valve seal of the inlet connector assembly.

FIGS. 18A-B depicts an inlet valve seal 320 of the inlet connector assembly 300. The inlet valve seal may have a body 322. The body 322 may define a connection rim 324 configured to integrate the inlet valve seal 320 with the inlet valve 330. The body 322 may also define a sealing rim 326 and an inlet valve external portion 328. The external portion 328 may define the entire portion of the inlet valve seal 320 that is exposed to the surrounding environment when the outlet connector assembly 300 is in a disconnected, closed state. To maintain an aseptic connection, the external portion 328 will generally be sealed from contact with any fluid passageway when the connector system 100 is in the connected, open state. For instance, the external portion 328 of the inlet valve seal 320 can be made to contact with the external portion 266 of the outlet valve seal 260 when the connector system 100 is in the connected, open state. In this way, the external portions 328, 266, which are exposed to the surrounding environment when the connector system 100 is in a disconnected state, are sealed from the fluid pathway when the connector system 100 is in the connected, open state. This seal of the external portions 328, 266 together maintains an aseptic connection for the fluid pathway.

The inlet seal valve external portion 328 may be configured to integrate with the outlet valve external portion 266. For instance, the external portions 328, 266 may have patterned protrusions and recessions configured to interlock. The general shape and size of the external portions 328, 266 may be identical. This may allow the external portions 328, 266 to seal themselves off from the fluid contact when in a connected state. In this manner, the external portions 328, 266 may be located within, but not exposed to, a given fluid passageway. As a result, the fluid connection may be aseptic so as not to contaminate or otherwise compromise the fluid passing through the connector system 100 when in the connected, open state.

Figure 19A:
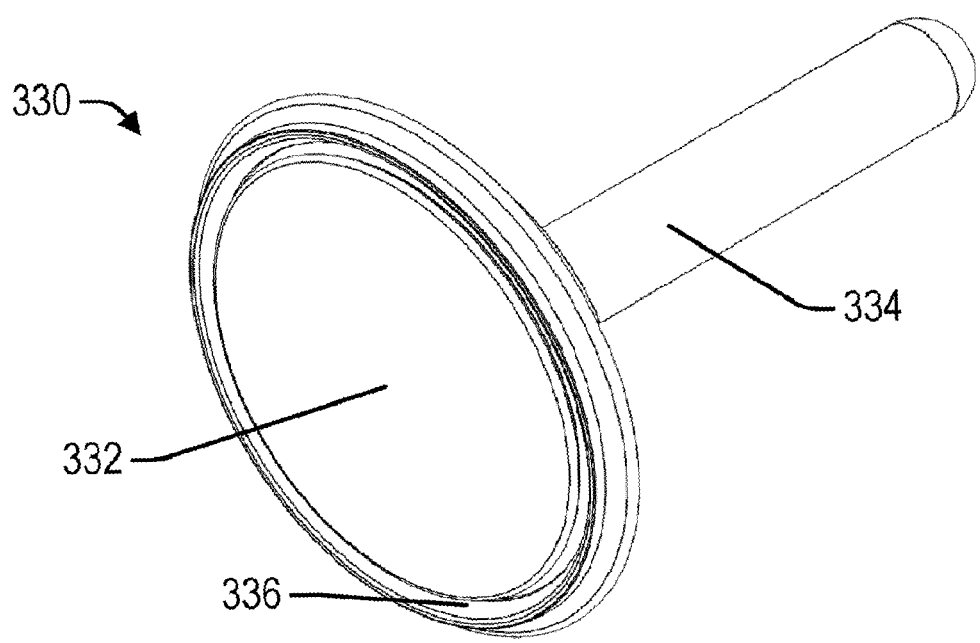
FIG. 19A is a front isometric view of an illustration of an inlet valve of the inlet connector assembly.
Figure 19B:
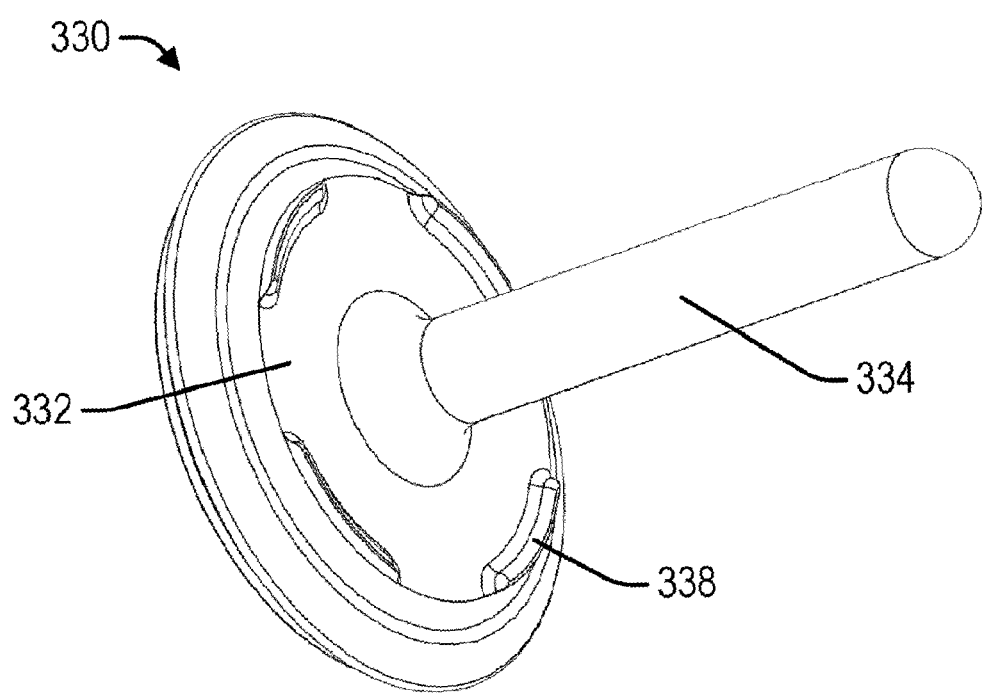
FIG. 19B a back isometric view of an illustration of an inlet valve of the inlet connector assembly.

FIG. 19 depicts an inlet valve 330 of the inlet connector assembly 300. The inlet valve 330 may have a body 332. The body 332 may define a shaft 334 configured to control the movement of the inlet valve 330. The shaft 334 may confine the movement of the inlet valve 330 to within the orifice of the spring 360. Consequently, the inlet valve 330 may constantly remain under force from the spring 360. This spring force may allow the inlet connector assembly 300 to remain in closed state when no additional forces are acting upon the inlet valve 330. When in a connected, open state, the outlet valve 260 may provide such an additional force on the inlet valve 330. The body 332 may also define a plurality of guide members 338 configured to guide the movement of the inlet valve 330 in relation to the inlet plenum 340. The inlet valve 330 may also have an opening 336 for receiving the connection rim 324 of the inlet valve seal.

Figure 20:
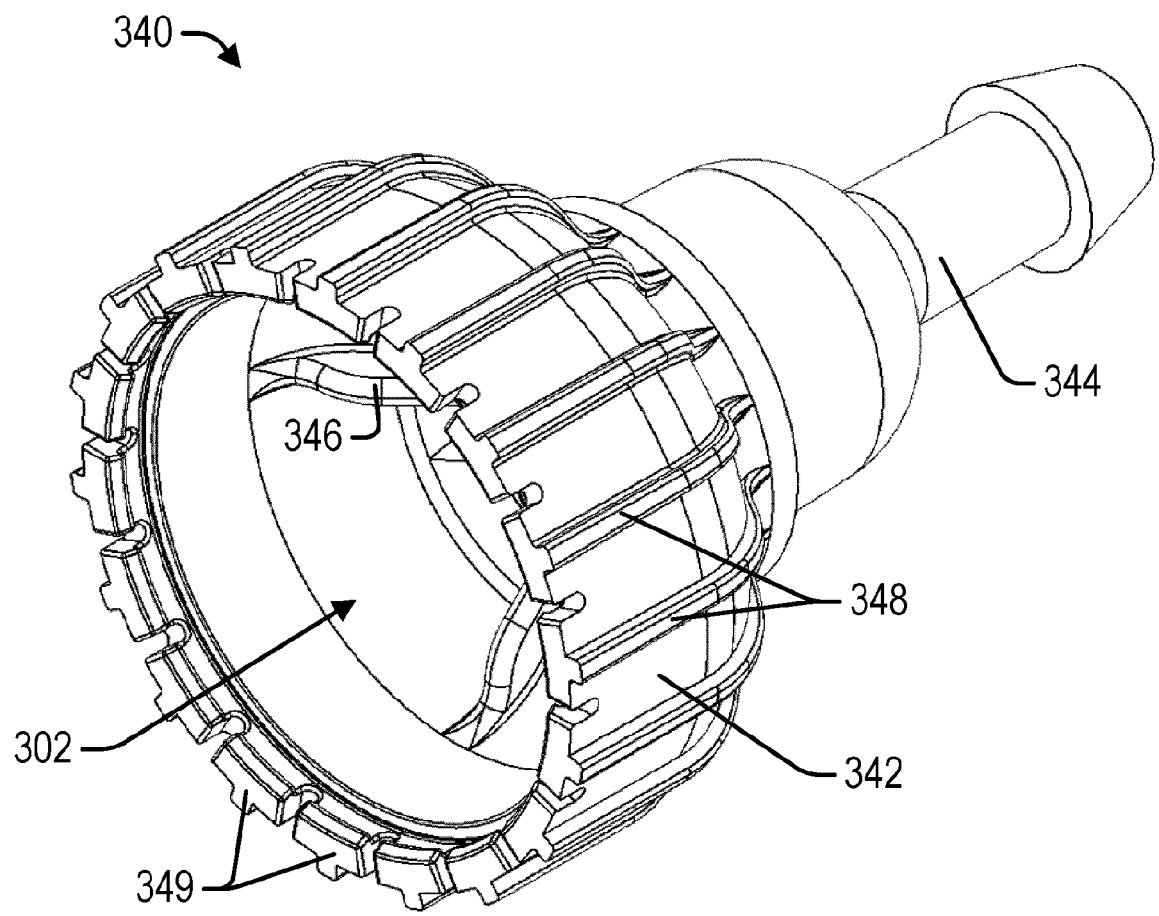
FIG. 20 is an isometric view of an illustration of an inlet plenum of the inlet connector assembly.

FIG. 20 depicts an inlet plenum 340 of the inlet connector assembly 300. The inlet plenum may have a body 342 defining an inlet fluid passageway 302. The body 342 may have an inlet tubing connector 344 which may function to provide a fitting to connect the inlet fluid passageway 302 with an external tube or conduit. The body may have a plurality of guide protrusions 346 configured to contact the guide members 338 of the inlet valve 330 and guide the movement of the inlet valve 330. The inlet plenum 340 may have a plurality of grip elements 348 which may allow a user to easily grip the inlet plenum 340 without the risk of slippage. The inlet plenum 340 may have a plurality of snap teeth 349 configured to couple to the recessed rim 314 of the inlet connector 310, thereby integrating the inlet plenum 340 and the inlet connector 310. In order to ensure a fluid impermeable seal, a gasket 350 may be placed in between the inlet plenum 340 and the inlet connector 310. The gasket 350 may be a standard o-ring or a similar seal.

In some embodiments, the inlet valve 330 may include an inlet valve seal 320 that has a sealing 326 rim configured to undergo a change in orientation when the connector system 100 changes state. The change in orientation of the sealing rim 326 may be an angular flip of at least 10, 20, 30, 40, 50, 60, 70, 80, 90, 120, 150, or 180 degrees. As a result of this change in orientation, the sealing rim 326 may also undergo a change in shape. The outlet connector 200 may also include an outlet valve 260 having an outlet valve seal 250 that has a sealing rim 254 configured to undergo a change in orientation when the connector system 100 changes state. The change in orientation of the sealing rim 254 of the outlet valve seal 250 may be an angular flip of at least 10, 20, 30, 40, 50, 60, 70, 80, 90, 120, 150, 180, 190, 200, 210, 220, 230, 240, or 270 degrees.

FIGS. 21A-G depict how the change in orientation of the sealing rim 326 of the inlet valve seal 320 and the sealing rim 254 of the outlet valve seal 250 may advantageously provide reusable aseptic connection. In FIG. 21A, the connector system 100 is shown in a disconnected, closed state. FIG. 21B shows the connector assemblies 200, 300 being brought together to the connected closed state of FIG. 21C. The exterior portions 266, 328 of the connector assemblies 200, 300 remain isolated from the fluid; however, the valve faces and the annular region around the connector openings must be sealed as well in order to maintain internal sterility. In FIG. 21D, the outlet valve seal 250 provides pressure on the inlet valve 330 and begins the transition to the open state. As the inlet valve 330 is opened the outlet valve seal 250 and inlet valve seal 320 are pushed towards their fully open positions. The connector assemblies 200, 300 may have shoulders that are molded into the outlet connector 200 and inlet connector 300 to facilitate this angular change. In FIG. 21E, the connector system 100 is in a fully open position. The inlet valve seal 320 may wrap around the septic face of the outlet valve 260, ensuring that all surfaces in contact with the fluid remain aseptic. The inlet and outlet valve seals 250, 320 may snap into this position once the shoulders push them over a critical equilibrium point due their Gaussian curvature. These inlet and outlet valve seals 250, 320 may be injection molded in their "open" positions so that they tightly seal against their respective faces to isolate the fluid even at pressure.

FIG. 21F shows the inlet and outlet valve 260, 330 coupling returning to a closed state. As the inlet valve 330 is closed, the inlet and outlet valve seals 250, 320 are pushed against one another by the spring force from the spring 360. As the seal face contact pressure is greater than the fluid pressure, the contact deformation of the seals 250, 320 squeezes the fluid out from between the seals 250, 320. As the inlet valve 330 continues to close, the inlet and outlet connector seal rims 254, 326 may be pushed back into their closed position by an opposing pair of shoulders, only once they cross back over their Gaussian curvature equilibrium point. This seal face contact as they slide back into their closed positions causes the fluid either side to be pushed back into either the inlet or outlet fluid passageways, with no fluid left in between. FIG. 21G shows the inlet and outlet valve 260, 330 coupling fully returned to a closed, connected state.

In one aspect, a method for providing aseptic fluid connection is provided. The method can generally comprise providing an inlet connector assembly, providing an outlet connector assembly, coupling the inlet valve to the outlet valve; and forming an aseptic fluid connection between the inlet and outlet fluid passageways when in a connected state. This method may be performed by a user using either two hands or one hand.

Figure 22A:
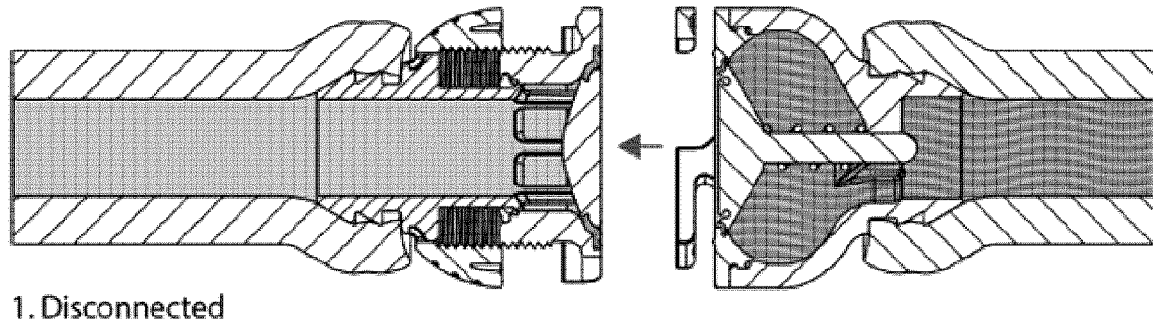
FIGS. 22A-E are schematic illustrations of the stages of movement of the inlet and outlet connector assembly components as the connector system transitions from a disconnected, closed state (FIG. 22A) to a connected, open state (FIG. 22D), and then begins the transition back to a connected, closed state (FIG. 22E).
Figure 22B:
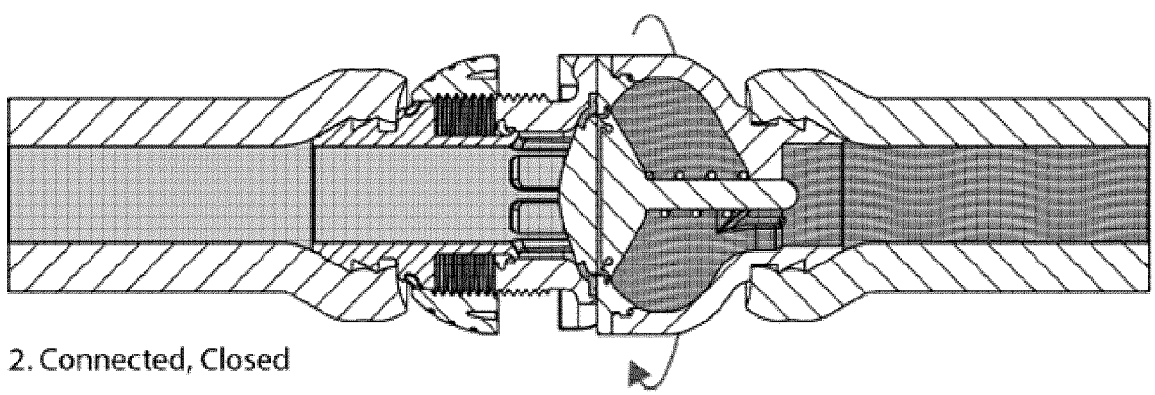
Figure 22C:
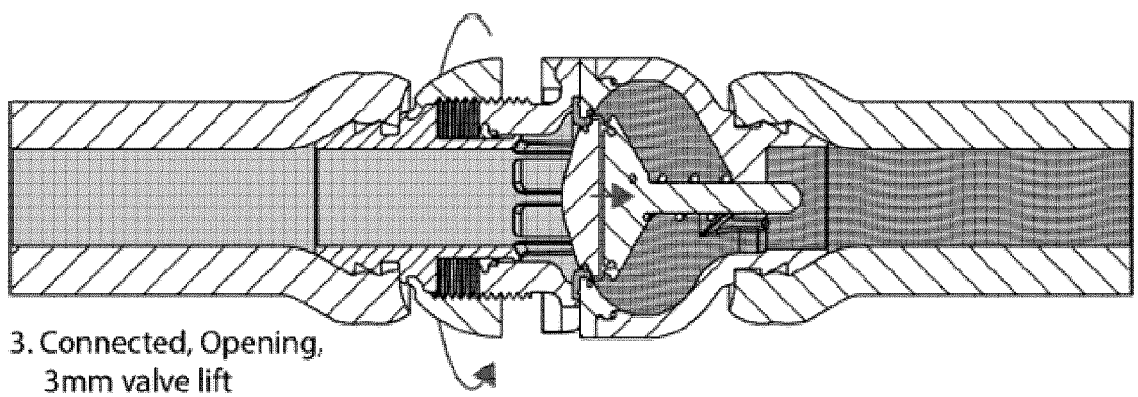
Figure 22D:
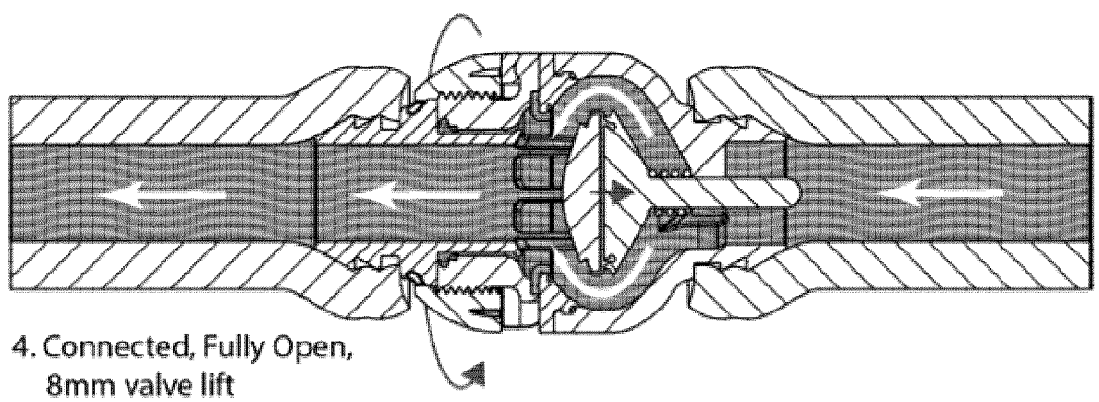
Figure 22E:
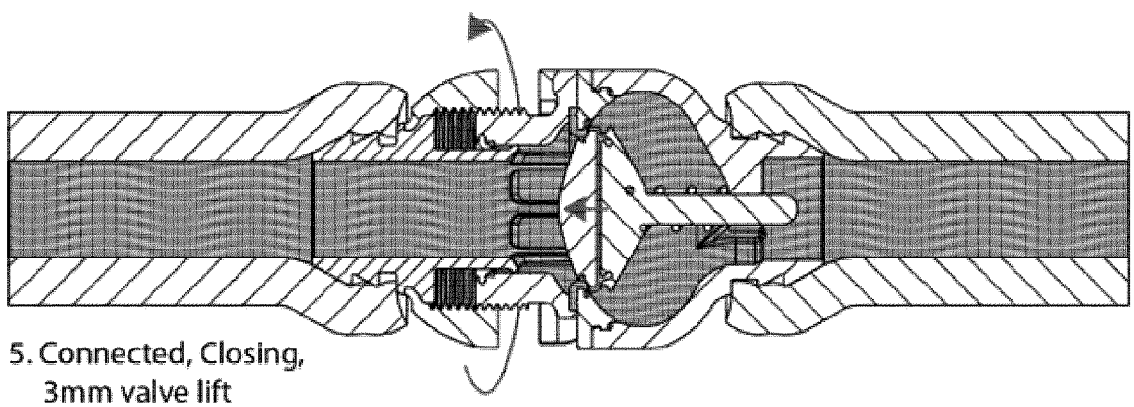

FIGS. 22A-E depict an embodiment of the method for providing aseptic fluid connection. In FIG. 22A, an inlet connector assembly and an outlet connector assembly are provided. The step of coupling the connector assemblies is shown in FIGS. 22A-B, where the connector assemblies are contacted and twisted to lock the mating components together. The step of forming an aseptic fluid connection is shown in FIGS. 22C-D where the thumbwheel is rotated to move the inlet and outlet valve coupling. The method may comprise an additional step of ceasing the aseptic fluid connection between the inlet and outlet fluid passageways, which is shown in FIG. 22E.

In another aspect, a method of making the connection system of the present disclosure is provided. The method can include forming the components of the connection system and assembling the components. Forming the individual components may include injection molding the components.

The outlet connector/outlet valve seal as well as the inlet valve/inlet valve seal pairings may be manufactured using multi-shot injection molding so that the seals are integral to the solid parts to ensure pressure sealing and aseptic operation. By forming the components in this manner, the assembly process may be simplified, allowing automated assembly to be considerably cheaper and faster. As discussed above, these seals can be molded in the "Open" position shown above so that their Gaussian curvature ensures that this is the shape they naturally return to.

The connectors, valves, outlet tube, thumb wheel, and inlet plenum may be formed from a suitable polymer or metal. For instance, these components may be formed from high-heat polycarbonate. The seals may be formed from a suitable polymer, such as silicone. The connector system may be formed from components that are all compatible with autoclave, ethylene oxide, and gamma sterilization techniques. All components of the connector system may be biocompatible with most chemicals and contain no leachables, extractables, or materials of animal origin.

Assembling the components may include assembling the inlet connector assembly separate from the outer connector assembly. The inlet connector assembly may be assembled by the following steps: First, the inlet valve and spring are inserted into the inlet plenum. Second, the o-ring is installed on the inlet connector. Third, the inlet connector is pressed into the inlet plenum, squeezing the o-ring. The snap teeth on the inlet plenum may click into a groove on the inlet connector. This may ensure a tamper proof, aseptic seal for the lifetime of the inlet connector assembly.

The outlet connector assembly may be assembled from the following steps: First, the thumbwheel is pressed onto the outlet tube engaging the snap teeth. Second, the outlet tube is pressed through the outlet connector and seals. The snap teeth may engage corresponding snap recesses in the outlet valve locking them together.

Figure 23:
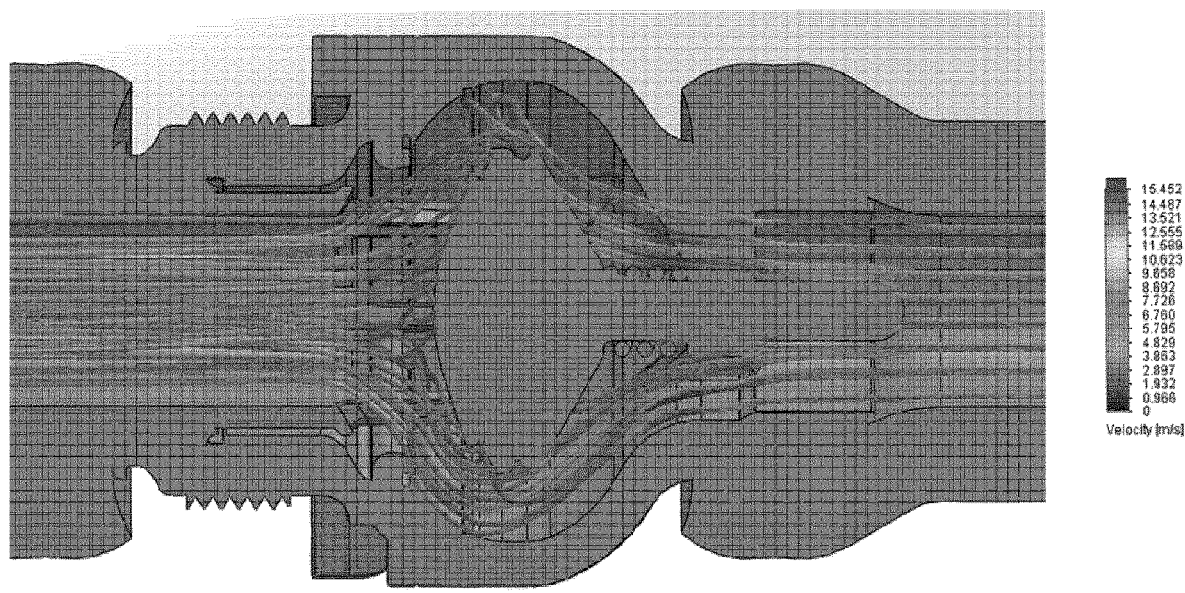
FIG. 23 is an example of a computer simulation of a dynamic pressure of the connector system in a connected, open state.

FIG. 23 depicts the results of a dynamic pressure test that was carried out. The test simulated a wide-open valve at 40 PSI assuming an exit pressure of 14.7 PSI (Standard Atmospheric Pressure). The fluid may be seen to accelerate around the valve support vanes and then slow down as it flows around the valve, regaining its original velocity as it passes through the outlet tube connector to the outlet.

Figure 24A:
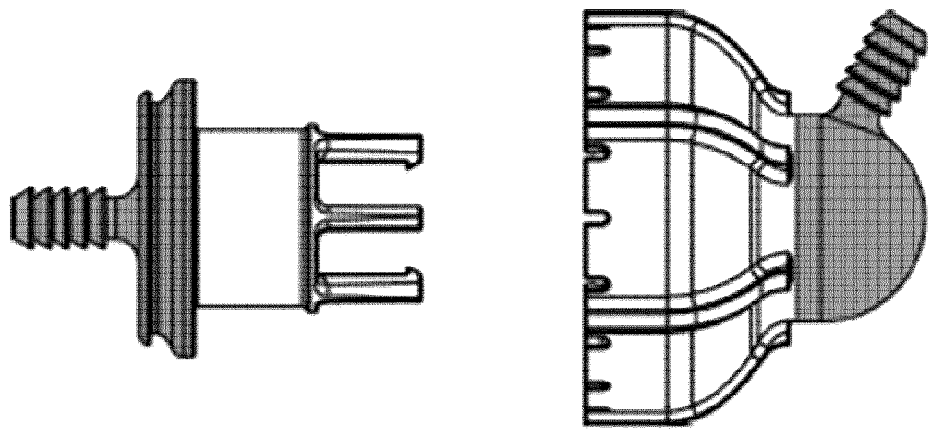
FIG. 24A is an isometric view of the connector system with small diameter inlet and outlet tubing connectors.
Figure 24B:
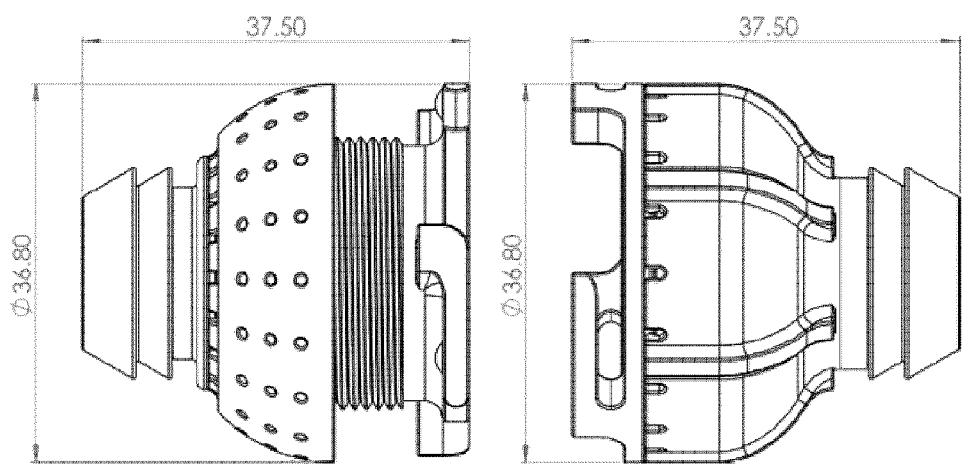
FIG. 24B is an isometric view of the connector system with large diameter inlet and outlet tubing connectors.

FIGS. 24A-B depicts various forms of the inlet and outlet tubing connectors as well as overall dimensions for one embodiment of the connector system. The tubing connectors may be configured to be compatible with all sizes of tubing. The tubing connectors may be specifically compatible with tubing sizes from 1/16 inch to 1/2 inch internal diameter. The tubing connectors may be sized to connect two different sized tubings. For example, the connector system may connect a 1/8 inch tubing line to a 1/4 inch tubing line. The tubing connectors may be barbed, push-fit, or of the sanitary tri-clamp type.

The present disclosure has described one or more preferred embodiments, and it should be appreciated that many equivalents, alternatives, variations, and modifications, aside from those expressly stated, are possible and within the scope of the invention.

The invention claimed is:

1. A connector system for providing an aseptic fluid connection, the connector system comprising:
an inlet connector assembly having an inlet fluid passageway and an inlet valve configured to seal the inlet fluid passageway when in a disconnected state; and
an outlet connector assembly having an outlet fluid passageway and an outlet valve configured to seal the outlet fluid passageway when in a disconnected state,
wherein the inlet valve is configured to couple to the outlet valve and move within the inlet fluid passageway or outlet fluid passageway to form the aseptic fluid connection between the inlet and outlet fluid passageways when in a connected state; and
wherein the outlet connector assembly is configured to provide adjustable movement of the coupled inlet valve and outlet valve to control a flowrate of fluid through the inlet and outlet fluid passageways and wherein the outlet connector assembly comprises a threaded thumbwheel for providing the adjustable movement.

2. The connector system of claim 1, wherein the inlet valve has an inlet valve external portion that is exposed to an external environment when in the disconnected state, and the outlet valve has an outlet valve external portion that is exposed to the external environment when in the disconnected state, optionally, wherein the inlet valve is configured to couple to the outlet valve in a manner that the inlet valve external portion and the outlet valve external portion are sealed from the inlet and outlet fluid passageways.

3. The connector system of claim 1, wherein the coupled inlet valve and outlet valve are configured to move in a predominantly linear direction, wherein the inlet connector assembly has a spring configured to provide a spring force to the inlet valve to seal the inlet connector assembly when in the disconnected state; wherein the inlet connector assembly and the outlet connector assembly are configured to be reusable and provide repeated aseptic connection and/or wherein the inlet connector assembly comprises an inlet tubing connector configured to connect to a tubing having a first internal diameter and the outlet connector assembly comprises an outlet tubing connector configured to connect to a tubing having a second internal diameter, wherein the first internal diameter is different in size from the second internal diameter.

4. The connector system of claim 1, wherein the inlet connector assembly is configured to couple to the outlet connector assembly to form the connected state, optionally wherein at least one of the inlet connector assembly and the outlet connector assembly comprise a locking feature configured to lock the inlet connector assembly and the outlet connector assembly together when in the connected state.

5. A connector system for providing an aseptic fluid connection, the connector system comprising:
an inlet connector assembly having an inlet fluid passageway and an inlet valve configured to seal the inlet fluid passageway when in a disconnected state; and
an outlet connector assembly having an outlet fluid passageway and an outlet valve configured to seal the outlet fluid passageway when in a disconnected state,
wherein the inlet valve is configured to couple to the outlet valve to form the aseptic fluid connection between the inlet fluid passageway and outlet fluid passageway when in a connected state;
wherein the inlet valve comprises an inlet valve seal that has a sealing rim configured to undergo a change in orientation when the connector assembly changes state; and
wherein the inlet connector assembly and the outlet connector assembly are configured to be reusable and provide repeated aseptic connection.

6. The connector system of claim 5, wherein the change in orientation of the inlet valve sealing rim is an angular flip of at least 50 degrees.

7. The connector system of claim 6, wherein the change in orientation of the inlet valve sealing rim is an angular flip of at least 100 degrees.

8. The connector system of claim 5, wherein the outlet valve comprises an outlet valve seal that has a sealing rim configured to undergo a change in orientation when the connector assembly changes state.

9. The connector system of claim 8, wherein the change in orientation of the outlet valve sealing rim is an angular flip of at least 50 degrees.

10. The connector system of claim 9, wherein the change in orientation of the outlet valve sealing rim is an angular flip of at least 100 degrees.

11. The connector system of claim 8, wherein the outlet valve seal has an annular shape.

12. The connector system of claim 5, wherein the coupled inlet valve and outlet valve are configured to move in a predominantly linear direction.

13. The connector system of claim 5, wherein the outlet connector assembly is configured to provide adjustable movement of the coupled inlet valve and outlet valve to control a flowrate of fluid through the inlet and outlet fluid passageways, optionally wherein the outlet connector assembly comprises a threaded thumbwheel for providing the adjustable movement.

14. The connector system of claim 5, wherein the inlet connector has a spring configured to provide a spring force to the inlet valve to seal the inlet connector assembly when in the disconnected state.

15. The connector system of claim 5, wherein the inlet connector assembly is configured to couple to the outlet connector assembly to form the connected state.

16. The connector system of claim 15, wherein at least one of the inlet connector assembly and the outlet connector assembly comprise a locking feature configured to lock the inlet connector assembly and the outlet connector assembly together when in the connected state.

17. The connector system of claim 5, wherein the inlet connector assembly comprises an inlet tubing connector configured to connect to a tubing having a first internal diameter and the outlet connector assembly comprises an outlet tubing connector configured to connect to a tubing having a second internal diameter, wherein the first internal diameter is different in size from the second internal diameter.

18. A method for providing an aseptic fluid connection, the method comprising:
providing an inlet connector having an inlet fluid passageway and an inlet valve configured to seal the inlet fluid passageway when in a disconnected state;
providing an outlet connector having an outlet fluid passageway and an outlet valve configured to seal the outlet fluid passageway when in a disconnected state; and
coupling the inlet valve to the outlet valve to form the aseptic fluid connection between the inlet fluid passageway and outlet fluid passageway,
wherein the inlet valve comprises an inlet valve seal that has a rim configured to undergo a change in orientation when the connector assembly changes state; and
wherein the inlet connector assembly and the outlet connector assembly are configured to be reusable and provide repeated aseptic connection.

* * * * *